United States Patent [19]

Waddell et al.

[11] Patent Number: 5,210,235

[45] Date of Patent: May 11, 1993

[54] METHODS OF ELABORATING ERYTHROMYCIN FRAGMENTS INTO AMINE-CONTAINING FRAGMENTS OF AZALIDE ANTIBIOTICS

[75] Inventors: Sherman T. Waddell, Westfield; Timothy A. Blizzard, Rahway, both of N.J.

[73] Assignee: Merck & Co., Inc., Rahway, N.J.

[21] Appl. No.: 936,176

[22] Filed: Aug. 26, 1992

[51] Int. Cl.$^5$ .......................................... C07D 315/00
[52] U.S. Cl. ...................................................... 549/415
[58] Field of Search ........................................ 549/415

[56] References Cited

U.S. PATENT DOCUMENTS

| | | |
|---|---|---|
| 3,869,444 | 3/1975 | Freiberg . |
| 3,923,784 | 12/1975 | Kierstead et al. ............... 536/7.4 |
| 3,979,511 | 9/1976 | Hung et al. . |
| 4,152,424 | 5/1979 | Kierstead et al. . |
| 4,328,334 | 5/1982 | Kobrehel et al. . |
| 4,349,545 | 9/1982 | d'Ambrieres et al. . |
| 4,464,527 | 8/1984 | Bright et al. . |
| 4,465,674 | 8/1984 | Bright et al. . |
| 4,492,688 | 1/1985 | Bright . |
| 4,512,982 | 2/1985 | Hauske et al. . |
| 4,517,359 | 5/1985 | Kobrehel et al. . |
| 4,518,590 | 5/1985 | Hauste et al. . |
| 4,526,889 | 7/1985 | Bright . |
| 4,680,386 | 7/1987 | Morimoto et al. . |
| 4,739,118 | 4/1988 | Elbe . |
| 4,886,792 | 12/1989 | Djokic et al. . |
| 4,921,839 | 5/1990 | Brain et al. . |
| 4,957,905 | 9/1990 | Hunt . |
| 4,990,602 | 2/1991 | Morimoto et al. . |

FOREIGN PATENT DOCUMENTS

| | | |
|---|---|---|
| 0101186 | of 0000 | European Pat. Off. . |
| 0109253 | of 0000 | European Pat. Off. . |
| 0136831 | of 0000 | European Pat. Off. . |
| 0259789 | of 0000 | European Pat. Off. . |
| 0283055 | of 0000 | European Pat. Off. . |
| 0298650 | of 0000 | European Pat. Off. . |
| 0307128 | of 0000 | European Pat. Off. . |
| 0316128 | of 0000 | European Pat. Off. . |
| 0340990 | of 0000 | European Pat. Off. . |
| 0342990 | of 0000 | European Pat. Off. . |

OTHER PUBLICATIONS

J. of Antibiotics, vol. 44, No. 3, pp. 313–329, by J. Gasc, et al., entitled *New Ether Oxime Derivatives of Erythromycin A: A Structure Activity Relationship Study* (1990).

Antimicrobic Newsletter, vol. 4, No. 4, pp. 25–36, by P. Fernandes, entitled *The Macrolide Revival: 35 Yrs. after Erythromycin* (Apr. 1987).

J. Org. Chem., vol. 39, No. 17, pp. 2492–2494, by R. Egan, et al., entitled *Configuration of 9-Imino Derivatives of Erythromycin* (1974).

J. of Antibiotics, vol. 40, No. 7, pp. 1006–1015, by S. Djokic, et al., entitled *Antibacterial in vitro evaluation of 10-kihydro-10-deoxo-11-azaerythromycin A: Synthesis & structure-activity Relationship of its Acyl Derivatives* (Jul. 1987).

J. Chem. Soc. Perkins Trans. 1 1986, pp. 1881–1890, by S. Djokic, et al., entitled *Erythromycin Series, Part 11, Ring Expression of Erythromycin A Oxime by the Beckmann Rearrangement*.

J. Chem. Research (S), 1988, pp. 152–153, by S. Djokic, et al., entitled *Erythromycin Series, Part 13, Synthesis and Structure Elucidation of 10-Dihydro-10-deoxo-11-methyl-11-azaerythromycin A*.

J. of Antibiotics, vol. XLI, No. 8, pp. 1029–1047, by G. Bright, et al., entitled *Synthesis, in vitro and in vivo activity of Novel-9-Deoxo-9a-Aza-9a-Homoerythromycin A Derivatives; of Macrolide Antibiotics, the Azalides* (Aug. 1988).

Tetrahedron Letters, No. 2, pp. 157–160, by E. Massey, et al., entitled *Erythromycylamine* (1970).

Chem. Abstracts, vol. 98, No. 17001, p. 542 (1983) (CA 98: 17006e).

*Primary Examiner*—Marianne M. Cintins
*Assistant Examiner*—John D. Peabody, III
*Attorney, Agent, or Firm*—Frank P. Grassler; Joseph F. DiPrima; Richard C. Billups

[57] ABSTRACT

A method of making compounds of the formulae:

(Abstract continued on next page.)

5 Claims, No Drawings

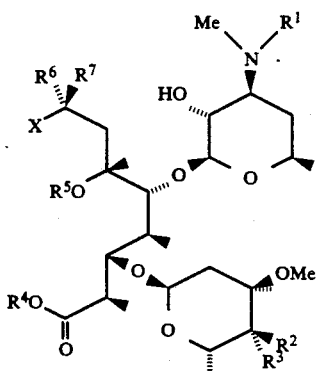 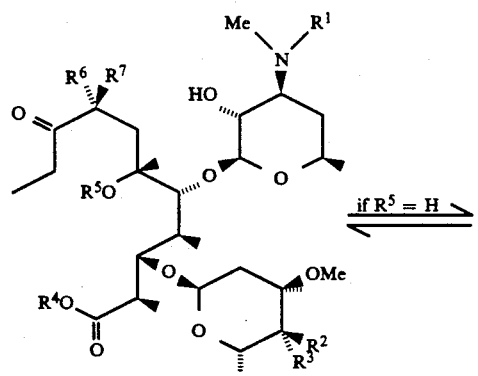

wherein
X is

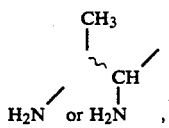

$R^1$ is hydrogen, methyl, $C_{1-10}$ alkoxycarbonyl or arylsulfonyl when X is $CH_3CH_2CHNH_2$ and is additionally aralkoxycarbonyl when X is $NH_2$; one of $R^2$ and $R^3$ is hydrogen and the other is OH, $NHR^1$ or $NMeR^1$ where $R^1$ is as defined above; $R^4$ is hydrogen or $C_{1-10}$ alkyl when X is $CH_3CH_2CHNH_2$ and is additionally aralkyl when X is $NH_2$; $R^5$ is hydrogen or $C_{1-3}$ alkyl when X is $CH_3CH_2CHNH_2$; $R^5$ is hydrogen when X is $NH_2$; one of R6 and R7 is hydrogen and the other is methyl except when X is $CH_3CH_2CHNH_2$ and $R^2$ is H, in which case $R^6$ is methyl and $R^7$ is hydrogen. These compounds are made from erythromycin-derived fragments of the formulae:

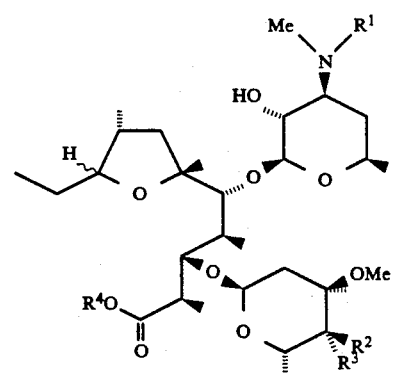

where $R^1$, $R^2$, $R^3$ and $R^4$ are defined as before for when X is $NH_2$; $R^5$ is hydrogen or $C_{1-3}$ alkyl; if $R^5$ is hydrogen, then $R^6$ is methyl and $R^7$ is hydrogen and the two structures above exist in equilibrium with each other; if $R^5$ is alkyl, then one of $R^6$ and $R^7$ is hydrogen and the other is methyl and the compound exists only as the structure on the above left.

METHODS OF ELABORATING ERYTHROMYCIN FRAGMENTS INTO AMINE-CONTAINING FRAGMENTS OF AZALIDE ANTIBIOTICS

BACKGROUND OF THE INVENTION

The present invention relates to a method of making intermediates useful in the synthesis of azalide antibiotics. Azalide antibiotics are useful in the therapy of bacterial infections in mammals.

The method begins with a fragment of the well known antibiotic macrocycle erythromycin A (Ia).

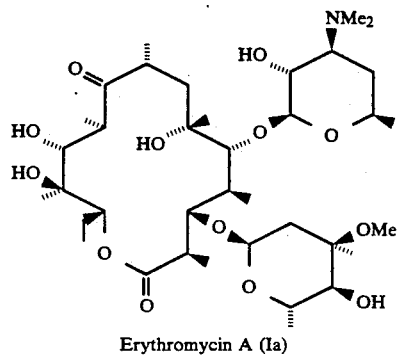

Erythromycin A (Ia)

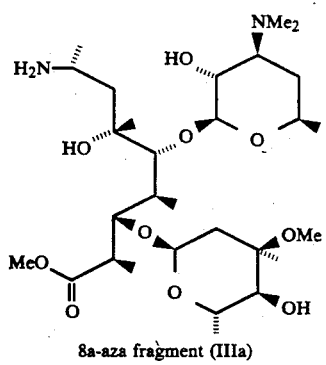

8a-aza fragment (IIIa)

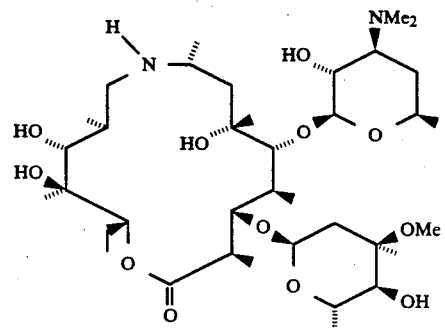

9-deoxo-8a-aza-8a-homoerythromycin A

Erythromycin A is cleaved to form an "eastern fragment" which consists of carbons 1 through 10 of the macrocycle.

The eastern fragment exists as an equilibrium mixture of ketone (IIa) and hemiketal (IIb) forms as shown:

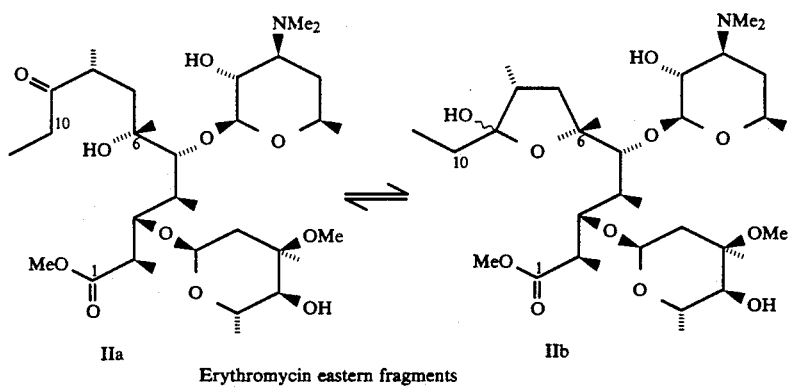

Erythromycin eastern fragments

The invention comprises a method of converting the prototypical erythromycin fragment(s) into a fragment (hereinafter referred to as the 8a-aza fragment) which is structurally homologous to the azalide antibiotic 9-deoxo-8a-aza-8a-homoerythromycin A, or alternatively into a fragment (hereinafter called the 9a-aza fragment) which is structurally homologous to the azalide antibiotic 9-deoxo-9a-aza-9a-homoerythromycin A. This homology is exact in the case of the 8a-aza fragment and 9-deoxo-8a-aza-8a-homoerythromycin A, and nearly exact in the case of the 9a-aza fragment and 9-deoxo-9a-aza-9a-homoerythromycin A (differing only in the presence of an ethyl group at C9 of the 9a-aza fragment) as can be seen in the formulae which follow:

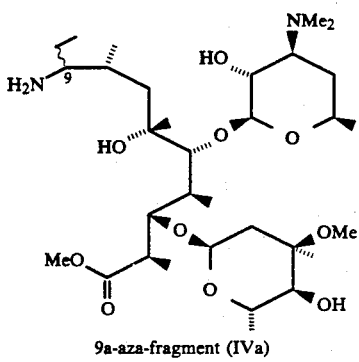

9a-aza-fragment (IVa)

-continued

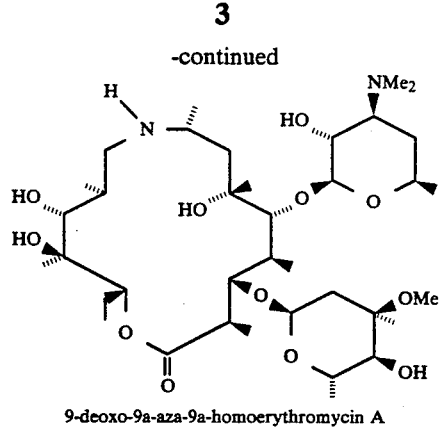

9-deoxo-9a-aza-9a-homoerythromycin A

These fragments are useful intermediates in the synthesis of azalide antibiotics which have high structural homology to 9-deoxo-8a-aza-8a-homoerythromycin A and 9-deoxo-9a-aza-8a-homoerythromycin A in their "eastern" sides, but which are free to diverge in structure by an arbitrary amount in their "western" sides (western side shall be understood to be any portion of the macrocyclic ring not part of the eastern side, as eastern is defined above).

SUMMARY OF THE INVENTION

The invention comprises a method of synthesizing amine product compounds of the formula

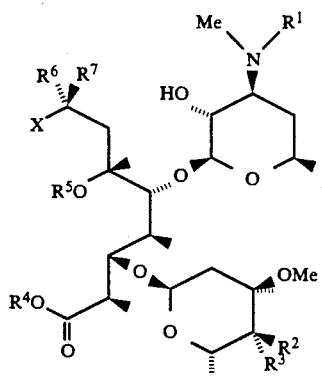

wherein
X is an amine of the formulae

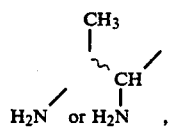

$R^1$ is hydrogen, methyl, $C_{1-10}$ alkoxycarbonyl or arylsulfonyl when X is $CH_3CH_2CHNH_2$ and is additionally aralkoxycarbonyl when X is $NH_2$;

one of $R^2$ and $R^3$ is hydrogen and the other is OH, $NHR^1$ or $NMeR^1$ where $R^1$ is as defined above;

$R^4$ is hydrogen or $C_{1-10}$ alkyl when X is $CH_3CH_2CHNH_2$ and is additionally aralkyl when X is $NH_2$;

$R^5$ is hydrogen or $C_{1-3}$ alkyl when X is $CH_3CH_2CHNH_2$;

$R^5$ is hydrogen when X is $NH_2$;

one of $R^6$ and $R^7$ is hydrogen and the other is methyl except when X is $CH_3CH_2CHNH_2$ and $R^5$ is hydrogen, in which case $R^6$ is Me and $R^7$ is H;

said method comprising the steps of (1) cleaving an erythromycin-like compound of the formula

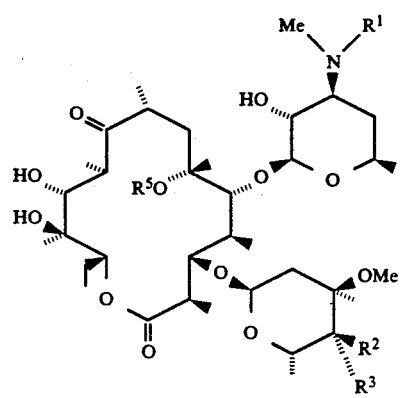

where $R^1$, $R^2$, $R^3$ are as defined before for when X is $NH_2$ and $R^5$ is hydrogen or $C_{1-3}$ alkyl, to produce compounds of the formulae

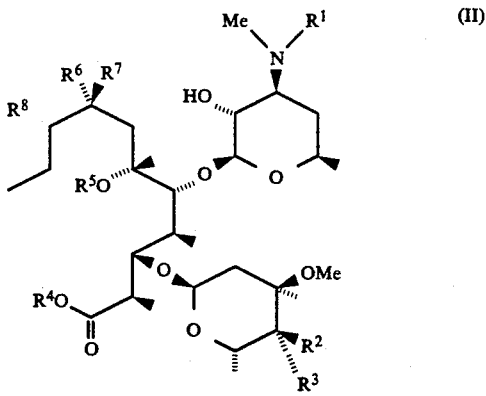

(II)

where $R^1$, $R^2$, $R^3$, $R^4$, $R^6$ and $R^7$ are as defined above for when X is $NH_2$, $R^5$ is hydrogen or $C_{1-3}$ alkyl when $R^8$ is oxo, $R^5$ is a covalent bond to the C-9 carbon atom when $R^8$ is hydroxyl, $R^8$ is oxo when $R^5$ is hydrogen or alkyl and $R^8$ is hydroxyl of either stereochemical orientation when $R^5$ is a covalent bond to the C-9 carbon atom;

(2) converting the product of step (1) into an oxime V of the formula

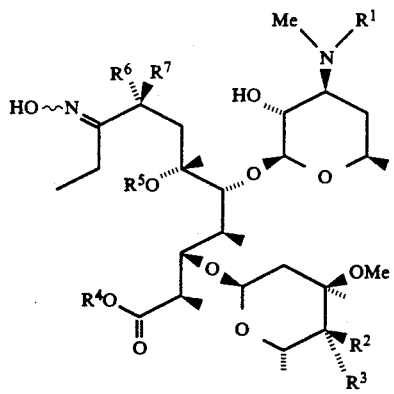

V where $R^1$, $R^2$, $R^3$, $R^4$, $R^6$, and $R^7$ are as defined above for when $X=NH_2$ and $R^5$ is hydrogen or $C_{1-3}$ alkyl; and (3) elaborating the oxime product of step (2) to said amine product compounds III and IV as defined below.

With respect to compound IV, reduction of this oxime produces the 9a-aza fragment (IV) directly.

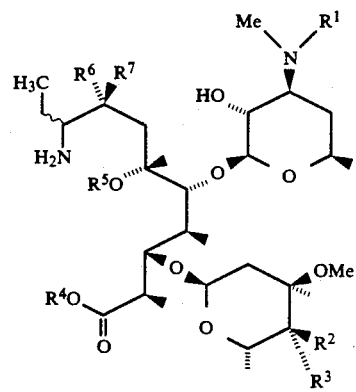

IV where $R^1$ through $R^7$ are as defined above for $X=CH_3CH_2CHNH_2$.

With respect to compound III, subjection of the oxime to a Beckmann rearrangement with intramolecular trapping of the intermediate cation by the C6 hydroxy group yields an imino ether that can be reductively cleaved to yield the 8a-aza fragment (III).

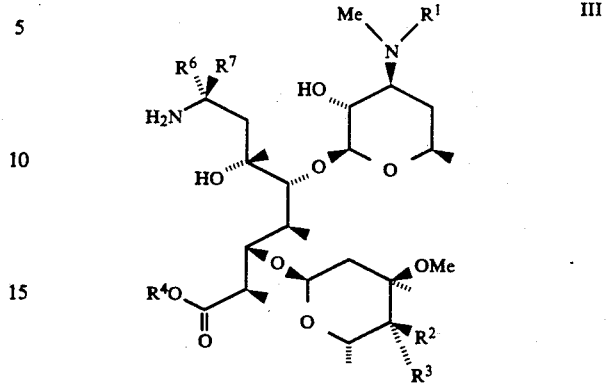

III where $R^1$ through $R^4$, $R^6$ and $R^7$ are as defined above for when X is $NH_2$.

The products III and IV can be readily prepared according to the following flow charts, detailed descriptions, examples, and modifications thereof, using readily available starting materials, reagents and conventional synthesis techniques. The overall process is illustrated in the following flow sheet. In these reactions it is also possible to use variants that are themselves known to those of ordinary skill in this art, but which are not mentioned in greater detail.

These flow charts and details likewise serve to illustrate the subsequent utility of the 8a-aza and 9a-aza fragments made by the process of the present invention.

In flow charts 1 and 2, it will be seen that X, $R^1$, $R^2$, $R^3$, $R^4$, $R^5$, $R^6$ and $R^7$ are as defined previously; $R^8$ is hydrogen, arylsulfonyl, $C_{1-10}$ alkyl or fluoroalkyl; Y is O, $NR^1$ or $CH_2$; A is a chain of 2–7 carbon atoms which may contain unsaturation or be interrupted by a heteroatom or a heterocycle or aromatic ring and which may bear a combination of the following substituents: hydrogen, alkyl, aryl, aralkyl, $OR^9$ (where $R^9$ is hydrogen, alkyl, aryl, aralkyl or trialkylsilyl), $SR^{10}$ (where $R^{10}$ is hydrogen, alkyl, aryl, aralkyl or acyl), or $NR^{10}R^{11}$ (where $R^{10}$ and $R^{11}$ are individually hydrogen, alkyl, aryl, aralkyl or acyl), oxo, nitro, cyano or halogen.

FLOW CHART 1

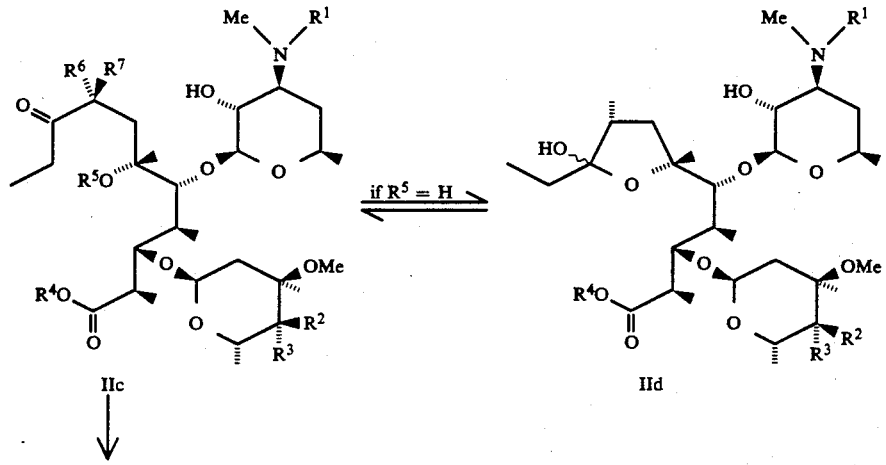

-continued
FLOW CHART 1
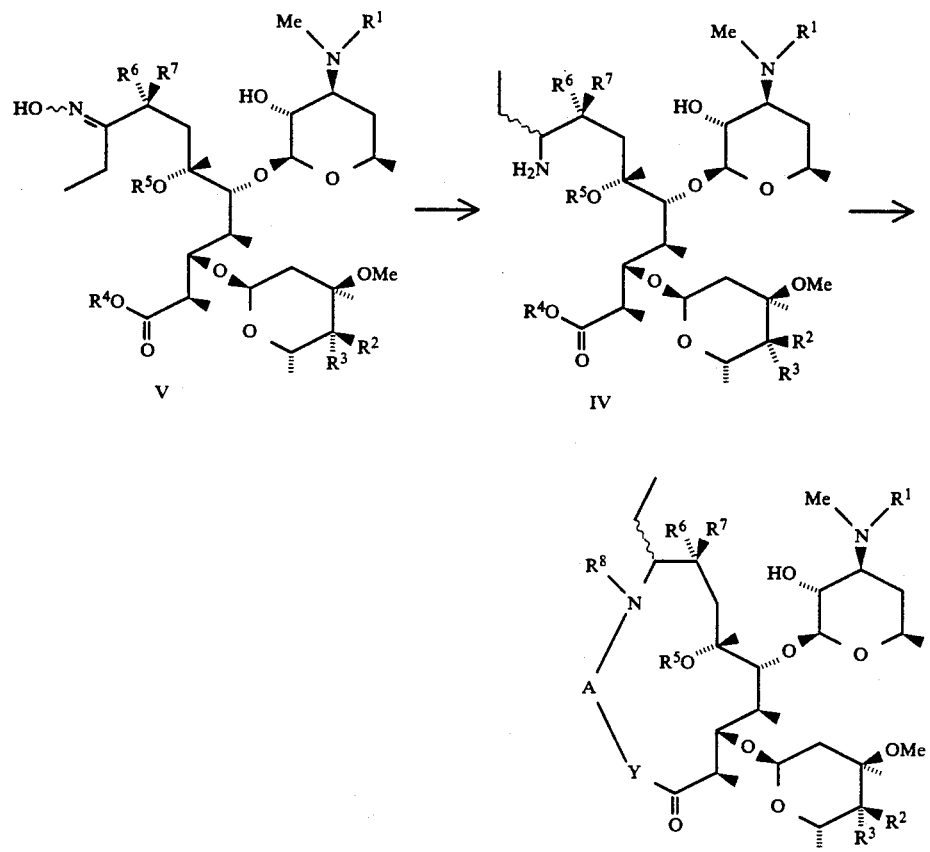
FLOW CHART 2
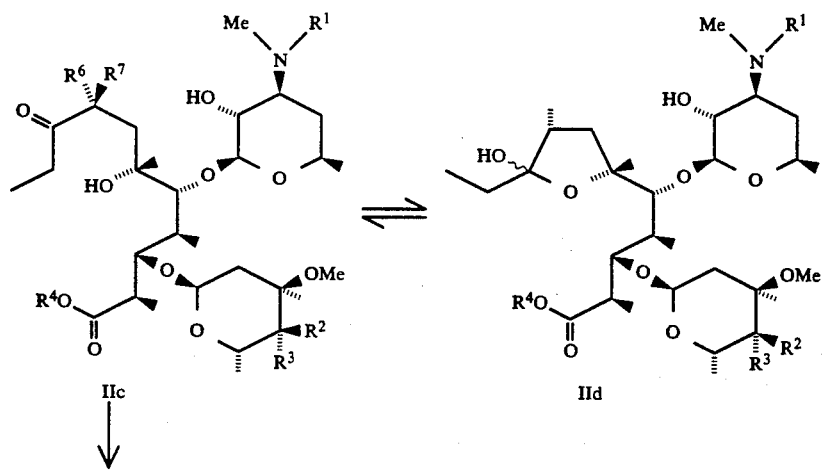

-continued
FLOW CHART 2

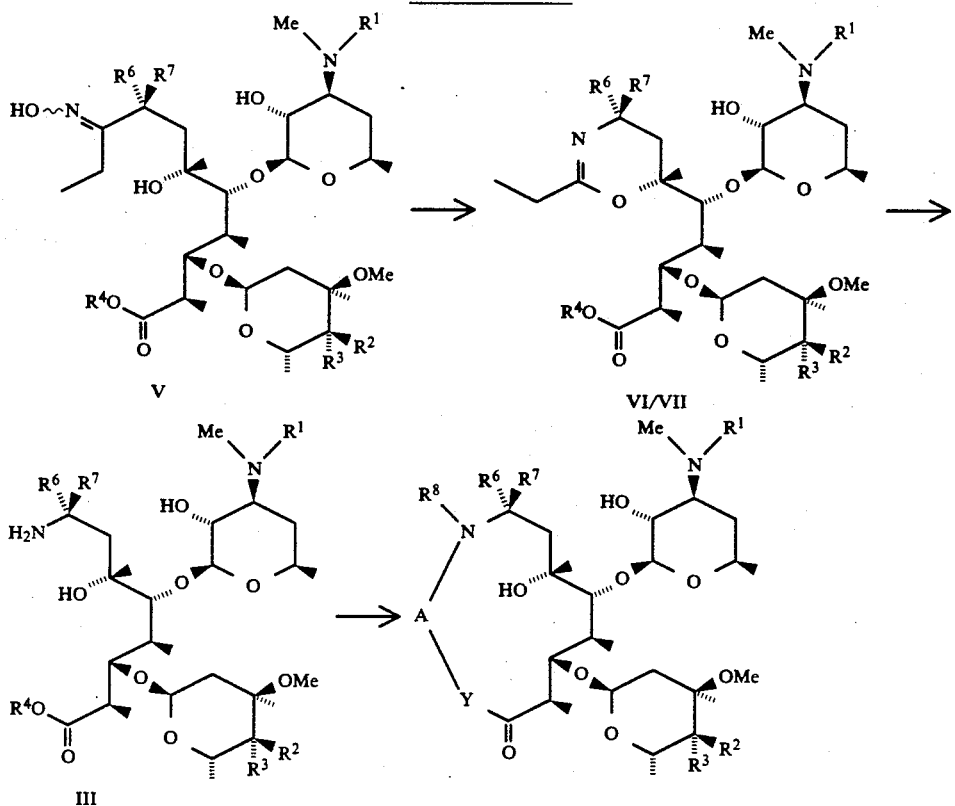

DETAILED DESCRIPTION OF THE INVENTION

The compounds III and IV can be prepared readily according to the following detailed descriptions and accompanying examples or modifications thereof using readily available starting materials, reagents and conventional synthesis procedures.

Appropriate starting materials for the fragmentation reaction include erythromycin and a large subset of its derivatives. The fragmentation is a retro-aldol process and requires the hydroxy function at position 11 and the ketone function (or other α-anion stabilizing function including but not limited to oximino, imino, hydrazono, etc.) at position 9. Modification of erythromycin at other sites should in general not affect the course of the fragmentation reaction.

Although not intending to be limited by a single theory of the invention, the fragmentation reaction is believed to occur by initial retro-aldol rupture of the C10-C11 bond and subsequent saponification of the ester function at carbon 1. The smaller fragment, comprised of carbons 11-13, can retroaldol further and/or polymerize under the reaction conditions, and is normally not isolated. The larger fragment, a carboxylate salt comprised of carbons 1-10 of the macrocycle, is essentially the sole isolated product of the reaction.

The retroaldol reaction is a well known base catalyzed reaction, and can in general be carried out with a large number of bases under a variety of reaction conditions. For derivatives of erythromycin the situation is complicated by the fact that several pathways for base catalyzed reaction exist. Most combinations of alkali and alkaline earth metal hydroxides and alkoxides in protic solvents give predominantly or exclusively another style of reaction and little or no retroaldol style reaction.

Preferably the retroaldol reaction is done in a polar aprotic solvent (most preferably THF but including and not limited to DMF, DMSO, DME, etc.) with a strong base which has good solubility in the chosen solvent (most preferably KOTMS but including and not limited to KOH, NaOH, LDA, etc.). Preferably the fragmentation reaction is carried out at a concentration of 0.01 to 0.10M, with 0.02M most preferred. The amount of base used is preferably from 1 to 10 equivalents based on starting material, with 5 to 6 equivalents most preferred. The reaction is usually run at a temperature of from 0° to 50° C., preferably at 22°-25° C. The reaction can be allowed to run from 2 hours to 35 days, but is preferably carried out over 6-18 hours.

The immediate product of the fragmentation reaction is a carboxylate salt, which is generally not isolated or purified but subjected immediately to conditions which form an ester at position 1. Esterification of a carboxylate can be accomplished in a very large number of ways, including but not limited to acid catalyzed condensation with alcohols and nucleophilic displacement on electrophilic alkyl species by the carboxylate ion. Acid catalyzed condensation is not preferrred for derivatives of erythromycin due to the potential labile nature of the attached carbohydrates under acid conditions, but if carefully optimized these methods could be used. Nucleophilic displacement by carboxylate on species of the general form R-X where R is a suitable alkyl group and X is a leaving group (including but not limited to Cl, Br, I, N$_2$, triflate, methanesulfonate, benzenesulfonate, tosylate, etc.) is the preferred method of esterification, and reaction with diazomethane is the most preferred of these methods. Because diazomethane must be protonated to form the active methyl diazonium species, the reaction mixture must be neutralized prior to reaction with diazomethane. For most other R-X species the derivatization can be carried out without prior neutralization.

Preferably the diazomethane reaction is done in an aprotic solvent (most preferably methylene chloride but including and not limited to DMF, DMSO, DME, ether, etc.) in which the neutralized (presumably zwitterionic) crude product of the fragmentation reaction is dissolved to a concentration of between 0.01M and 0.25M with 0.07M most preferred. A crude solution of diazomethane in a suitable solvent (preferably ether) is dripped in until the yellow color persists, and then after being allowed to stir from 5 minutes to one hour the excess diazomethane is quenched with a suitable carboxylic acid (preferably acetic acid). The reaction is usually run at a temperature of from 0° C. to 25° C., preferably at 22°-25° C.

EXAMPLE A

Preparation of an equilibrium mixture of 11, 12, 12a, 13, 14, 15-hexanorerythromycin A seco acid methyl ester and the two C-9 diasteriomeric 11, 12, 12a, 13, 14, 15-hexanorerythromycin A-6, 9-hemiketal seco acid methyl esters during which time the color changed from clear to greenish yellow, and a bit of fine precipitate formed and clung to the walls of the flask. At this time the reaction was judged to be complete by thin layer chromatography (silica plates, 93:7:1 $CH_2Cl_2$:MeOH:aq. $NH_3$ as eluent, p-anisaldehyde stain). The tetrahydrofuran was removed under vacuum and the residue was dried further under high vacuum at room temperature for 30 minutes. Next, 300 ml of water was added to the residue and the pH was adjusted to 7.0 using 2N HCl and monitoring continuously with a pH meter. The water was then removed under high vacuum. The residue was then triturated repeatedly with $CH_2Cl_2$, each time decanting the organic from the gummy salts (centrifugation can be used here if necessary.) When it was judged that all of the compound had been removed from the salts, the methylene chloride solution was dried with $MgSO_4$ and concentrated to about 250 ml.

Diazomethane was prepared from 4 g N-nitroso-N-methylurea, 12 ml 40% KOH and 100 ml ether in the manner described in Org. Syn. Coll, Vol, 2 165 (1943). This ether solution of diazomethane was poured into the methylene chloride solution of the carboxylic acid from above, and allowed to stir for 5 minutes, after which time acetic acid was added until the excess diazomethane was decomposed (as judged by the disappearance of the yellow color). TLC (silica plates, 93:7:1 $CH_2Cl_2$:MeOH:aq. $NH_3$ as eluent, p-anisaldehyde stain)

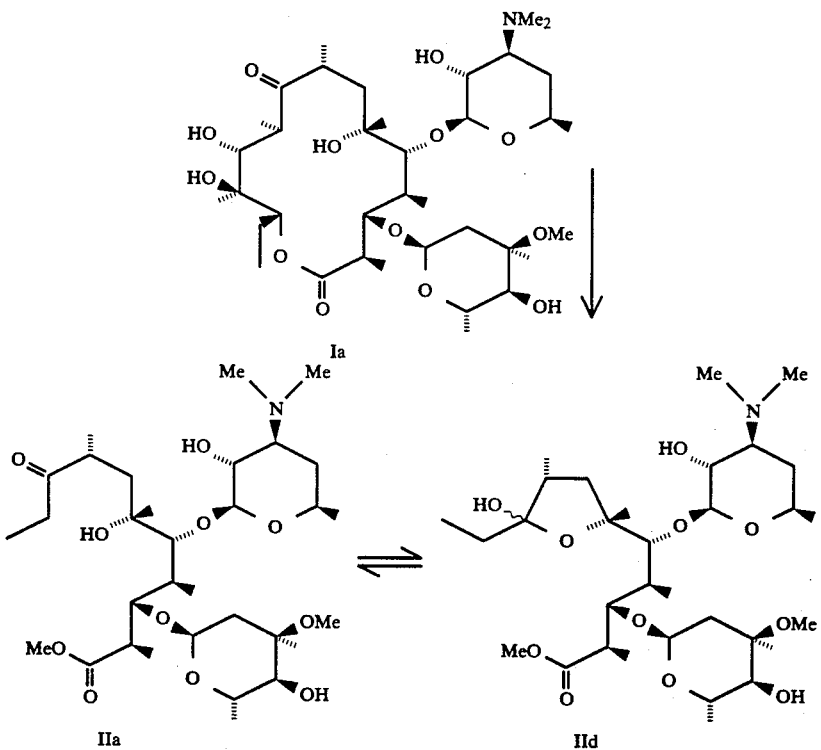

To a 2 L flask was introduced 10 g of erythromycin A (ca. 13.6 mmol, ca. 95% pure, available from Aldrich Chemical Company, Milwaukee, WI) and 10 g of tech. potassium trimethysilanoate (70 mmol, ca. 90% pure, available from Aldrich Chemical Company, Milwaukee, WI). The two powdery compounds were thoroughly mixed by agitation, and then 800 ml of Aldrich Sure-Seal tetrahydrofuran was poured quickly into the flask with shaking to insure rapid mixing. The reaction was allowed to stir at room temperature for three hours, at this point showed a major spot with an $R_f$ of approximately 0.6, along with a substantial baseline spot. Extraction with water effectively removed the baseline material, which could be reneutralized and subjected again to the diazomethane reaction. The organic layer was extracted with sat. aq. $NaHCO_3$, dried over $MgSO_4$, and rotovapped to yield 5.8 g of crude hemiketal. The product of this reaction was sufficiently pure to be used in a subsequent step, but could be further purified by flash chromatography on silica gel, eluting with 92:8:1 CH$_2$Cl$_2$:MeOH: aq, NH$_3$. NMR shows predominantly the hemiketal form of the product.

Selected spectral data:
$^1$H NMR (400 MHz, CDCl$_3$) δ 4.54 (d, H-1″), 4.47 (d, H-1′), 4.15 (dd, H-3), 3.96 (dq, H-5″), 3.63 (s, COOCH$_3$), 3.49 (m, H-5′), 3.26 (dd, H-2′), 3.24 (s, OCH$_3$), 2.93 (d, H-4″), 2.73 (dq, H-2), 2.50 (m, H-3′), 2.27 (s, N(CH$_3$)$_2$), 1.43 (d, H-2″ ax), 1.08 (d), 0.89 (t, CH$_3$-11),.
$^{13}$C NMR (CDCl$_3$) δ 176.6, 107.1, 102.6.

Synthesis of the 9a-Aza Fragment (IV)

The overall process for the synthesis of compound IV is shown as follows:

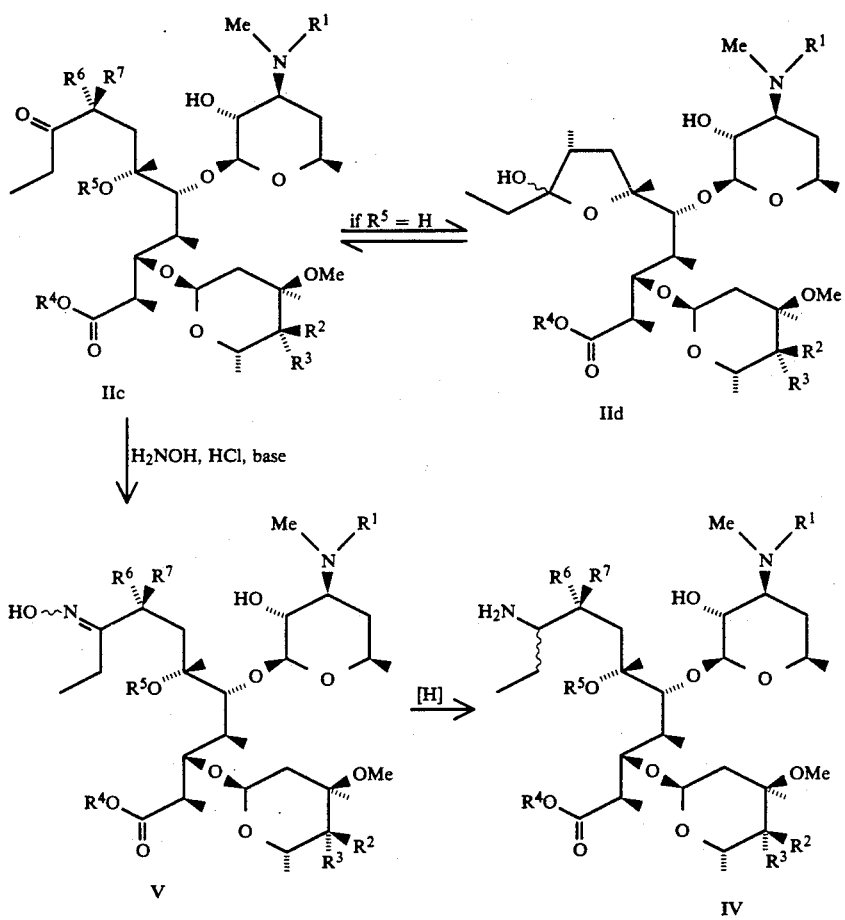

where R$^1$ is hydrogen, methyl, C$_{1-10}$ alkoxycarbonyl or arylsulfonyl or additionally aralkoxycarbonyl prior to the conversion step that yields product IV;
one of R$^2$ and R$^3$ is hydrogen and the other is OH, NHR$^1$ or NMeR$^1$ where R$^1$ is hydrogen, methyl, C$_{1-10}$ alkoxycarbonyl, arylsulfonyl or aralkoxycarbonyl; R$^4$ is hydrogen or C$_{1-10}$ alkyl or additionally aralkyl prior to the conversion step that yields product IV; R$^5$ is hydrogen or C$_{1-3}$ alkyl; when R$^5$ is hydrogen, then R$^6$ is methyl and R$^7$ is hydrogen and the two structures for the starting material IIc and IId exist in equilibrium with each other; when R$^5$ is C$_{1-3}$ alkyl, then one of R$^6$ and R$^7$ is hydrogen and the other is methyl and the starting material exists only as structure IIc.

The starting material for the sequence is the C1-C10 fragment (II) derived from erythromycin or one of its simple derivatives. When R$^5$ is alkyl, this fragment has a ketone function at C9 (IIc); when R$^5$ is hydrogen, this compound exists as an equilibrium mixture of the ketone (IIc) and the diastereomeric 6,9-hemiketal forms (IId). In general, the hemiketal form predominates in the mixture. Many derivatives of the ketone, however, are readily prepared from this mixture because the ketone is present in a finite, if small, amount and is constantly replenished as it is drained away.

The first step of the sequence involves preparation of the oxime from the ketone or ketone/hemiketal mixture. The conversion of ketones to oximes is an old and well known reaction and is not the invention as claimed below, but is rather one component of the invention. Although it has many variations in its details, it essentially involves exposing the ketone to hydroxylamine hydrochloride and a suitable base in a suitable solvent. The reaction is exothermic and proceeds readily. Preferably the reaction is carried out in pyridine, which acts as both the solvent and the base, but the combination of ethanol and an amine base such as triethylamine is also suitable. The concentration of starting material is preferably 0.01 to 0.5M with 0.1M most preferred. Preferably from 1 to 10 equivalents of hydroxylamine hydrochloride is used in the reaction, with 5 equivalents most preferred. The reaction is usually run at a temperature of from 22° C. to 50° C., with 25° C. most preferred. The reaction can be allowed to run from 5 hours to several days, but is usually complete within 6–18 hours.

The second step of the sequence involves reducing the oxime to the corresponding amine. This can be accomplished in a variety of ways. The preferred means is a high pressure catalytic hydrogenation (1000 psi $H_2$) using $PtO_2$ catalyst and acetic acid as solvent. The concentration of starting material is preferably 0.01 to 0.5M with 0.1M most preferred. Preferably from 0.1 to 1 weight equivalents of platinum oxide catalyst is used in the reaction, with 1 equivalent most preferred. The reaction is usually run at a temperature of from 22° C. to 50° C., with 25° C. most preferred. The reaction can be allowed to run from 16 to 48 hours, but is usually complete within 24 hours. In general, benzyl and substituted benzyl protecting groups for the carboxyl function as well as the benzyloxycarbonyl protecting group for the amines will be lost under the catalytic hydrogenation conditions required to reduce the oxime to a ketone.

A good alternative method for accomplishing this reduction is the combination of $TiCl_3$ and $NaH_3BCN$ described by Kirst and Leeds in Synthetic Communications, 18(8), 777 (1988), the disclosure of which is incorporated herein by reference. Still other means of carrying out this reduction include catalytic hydrogenation with other catalysts (particularly Pd/C or Raney Ni), dissolving metal reduction (particularly using Na, Na-Hg, or Al-Hg), or metal hydride reducing agents ($NaBH_4/TiCl_4$ or $NaBH_4/NiCl_2$.)

Synthesis of the 8a-Aza Fragment (III)

The overall process for the synthesis of amine fragment III is shown in flow charts 3, 4 and 5 (where $R^1$, $R^2$, $R^3$, and $R^4$ are as defined before) and begins with a Beckmann rearrangement of the oxime (prepared as described above.).

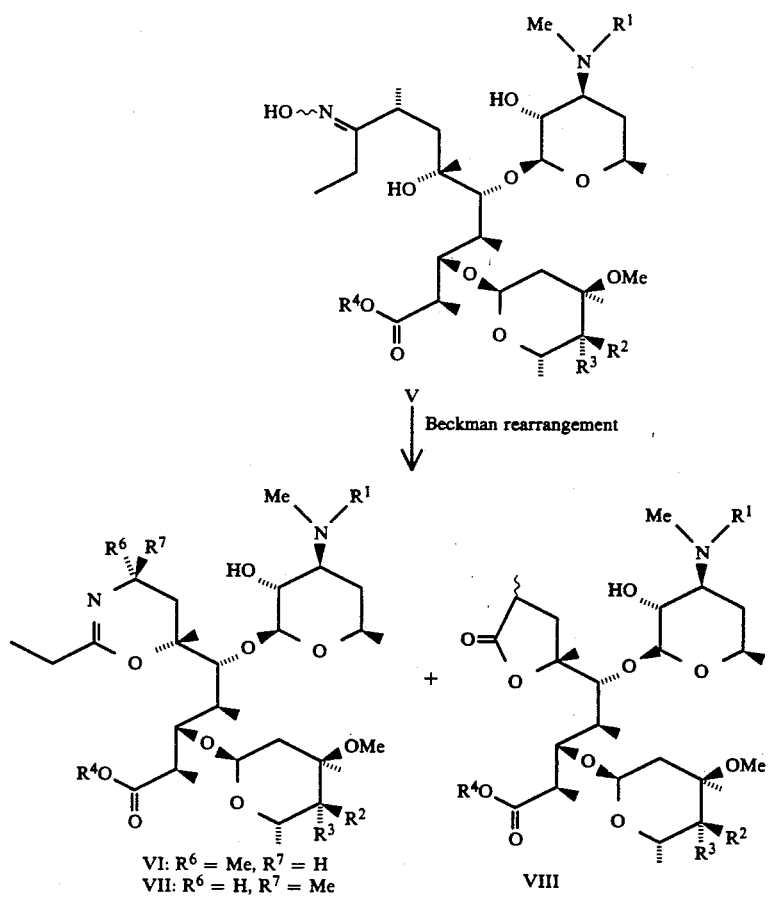

FLOW CHART 3

FLOW CHART 4

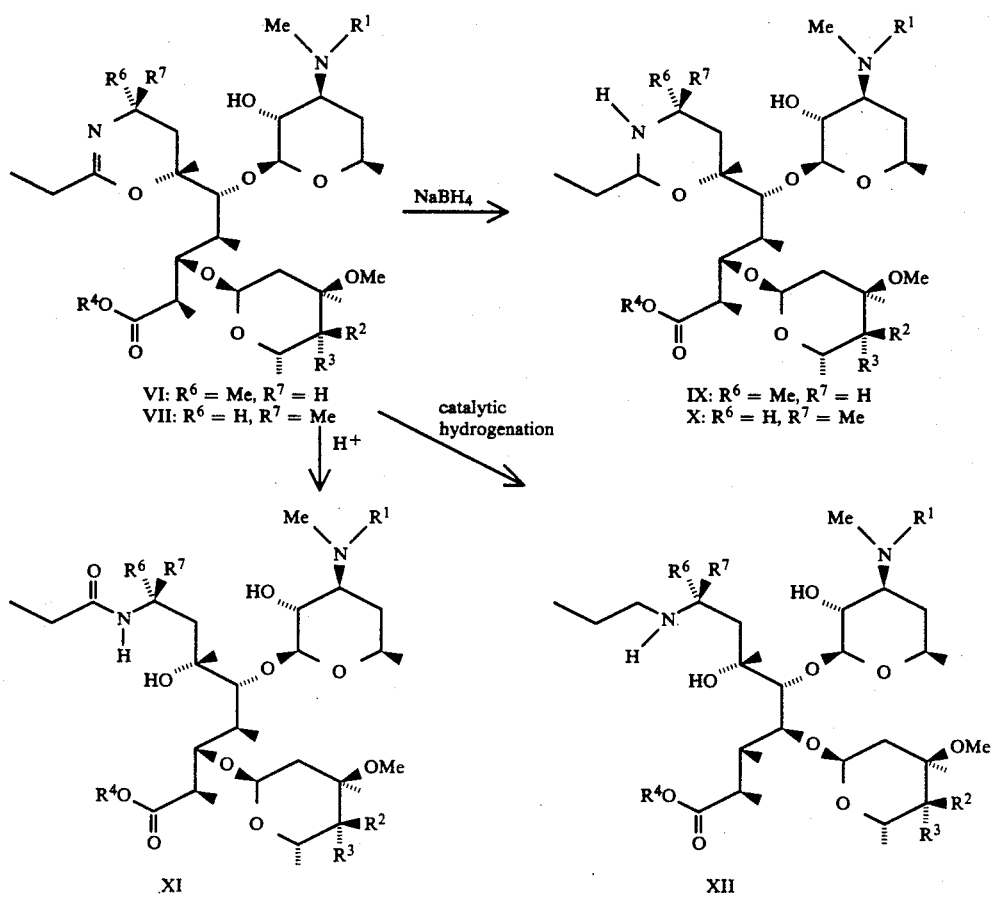

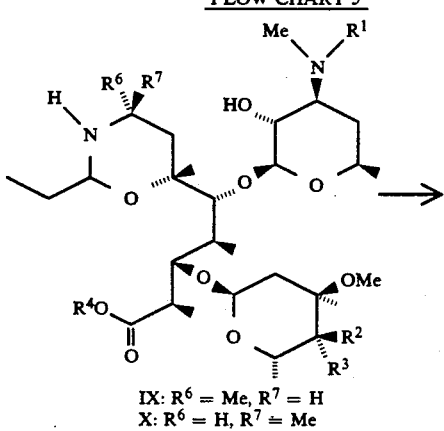

FLOW CHART 5

-continued
FLOW CHART 5

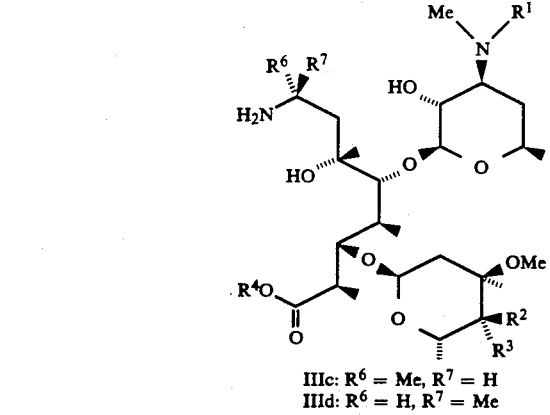

IIIc: $R^6 = Me$, $R^7 = H$
IIId: $R^6 = H$, $R^7 = Me$

In general, the Beckmann rearrangement of ketoximes leads to carboxamides. The mechanism involves initial conversion of the amine hydroxyl group to a leaving group which is lost with concommitant migration of the oxime carbon substituent that is situated anti to the leaving group. In aqueous media, the intermediate nitrilium cation thus formed usually is trapped by water to afford the amide product. The nitrilium intermediate can also be trapped by other nucleophiles, including intramolecular trapping by hydroxyl groups located elsewhere in the molecule.

Spectral data indicate that the oxime starting material V is predominantly a single stereoisomer, which based on simple steric arguments is presumably the E isomer. Beckmann rearrangement of the E isomer of V with trapping of the intermediate cation by the 6-OH gives rise to the major product, the cyclic iminoether VI. The C-8 epimeric iminoether VII presumably arises from initial epimerization of the E-oxime under the mild acidic conditions of the rearrangement as it is normally practiced. The mixture of C-8 epimeric lactones VIII presumbly arises from Beckmann rearrangement of the minor Z-oxime to form an unstable exocyclic iminoether, which hydrolyzes to the lactone during aqueous workup.

There are many ways to accomplish the Beckmann rearrangement under acidic, neutral or basic conditions (see "Comprehensive Organic Chemistry", I. O. Sutherland (ed.), Pergamon Press, N.Y., 1979, Vol. 2, pgs. 398–400 and 967–968). The most acidic conditions (which include concentrated sulfuric acid, polyphosphoric acid, thionyl chloride, phosphorus pentachloride, sulfur dioxide, and formic acid) are of little value here due to the sensitivity of the macrolide fragment (particularly the cladinose residue) to strong acid.

A preferred method for effecting the Beckmann rearrangement involves intial O-acylation of the oxime group with an alkylsulfonyl halide, arylsulfonyl halide, or arylsulfonic anhydride. The intermediate oxime sulfonate thus formed can be isolated or, as more commonly practiced, converted in situ to the rearranged products. The acylation and rearrangement reactions are generally performed in the presence of an organic or inorganic base.

Preferred acylating reagents for effecting the rearrangement of the oxime A include methanesulfonyl chloride, benzenesulfonyl chloride, 4-acetamidobenzene-sulfonyl chloride, p-toluenesulfonyl chloride, benzenesulfonic anhydride, and p-toluenesulfonic anhydride. The reaction can be carried out in the presence of an inorganic base (such as sodium bicarbonate or potassium carbonate) or an organic base such as pyridine, 4-dimethylaminopyridine, triethylamine, or N,N-diisopropylethylamine. Suitable solvents include anhydrous organic solvents such as dichloromethane, chloroform, ethyl acetate, diethyl ether, tetrahydrofuran, toluene, acetonitrile, and pyridine. Mixtures of organic solvents, especially those containing pyridine, are very useful. Aqueous mixtures such as aqueous acetone or aqueous dioxane are unsuitable because they favor formation of the amide XI. The reaction is generally performed using 1–5 molar equivalents of the acylating reagent and one or more molar equivalents of base at $-10°$ C. to $60°$ C. Pyridine can be used as both the solvent and the base.

The distribution of products resulting from the Beckmann rearrangement of oxime V depends on the particular reaction conditions employed. In general, treating a 0.05 to 0.1M solution of the oxime in pyridine with one equivalent of activating reagent (such as p-toluenesulfonyl chloride or p-toluenesulfonic anhydride) at room temperature leads to incomplete conversion of starting material to desired imino ether VI. If the reaction is conducted at $60°$ C. it proceeds essentially to completion, but with substantial formation of the lactone by-products VIII (along with a smaller amount of the epimeric by-product VII). Conducting the reaction at room temperature with 5 equivalents of the activating reagent also forces the reaction to near completion, but with substantial formation of epimeric by-product VII (along with smaller amounts of VIII.) The most preferred conditions for effecting this reaction involve treating a 1.3 to 1.5M solution of the oxime in pyridine with 1.1 equivalents of p-toluenesulfonyl chloride. At this greater concentration the reaction proceeds to very near completion with minimum formation of by-products.

It should be noted that the epimeric iminoether by-product VII is easily separated from iminoether VI by silica chromatography and is useful for the synthesis of the 8-S amino fragment IIId. To this end, the oxime can be initially epimerized with p-toluenesulfonic acid (or virtually any other acid) in pyridine, after which Beckmann rearrangement yields approximately a 50/50 mixture of VI and VII.

Conversion of iminoether VI into amine fragment IIIc (note that everything in the following discussion applies equally well to the conversion of iminoether VII to the amine fragment IIId) is not readily accomplished by simple acid hydrolysis, as this leads almost exclusively to the amide XI. Most methods of reduction similarly fail to provide the aminal IX or the amine IIIc. Catalytic hydrogenation (1000 psi $H_2$ with $PtO_2$ catalyst in acetic acid) furnishes the propylamine XII in good yield as the only product. Reduction of iminoether V with sodium borohydride at room temperature or at $pH<6$ also furnishes predominantly the propylamine XII.

The preferred means of reducing the iminoether VI to the aminal IX essentially follows the method developed by Myers et al and described in J. Org. Chem., Vol. 38, No. 1, p. 36, 1973. This preferred method involves cooling a solution of the iminoether VI (0.005M to 0.5M) in a 1:1 mixture of tetrahydrofuran and 95% ethanol to between $-35°$ C. and $-45°$ C., and then treating this solution with from 1 to 5 mole equivalents (3 most preferred) of sodium borohydride in a small amount of water. To this solution is then added 850 ml of 2N HCl for each millimole of sodium borohydride used. This produces a solution which "tests" as pH 6 to 7 when applied to damp pH paper. The reaction is allowed to stir for 4 to 24 hours at a temperature of between $-35°$ and $-45°$ C. Any lactone contaminant in the starting material is unaffected by this reaction.

The aminal IX produced in this manner is a single stereoisomer of uncertain configuration at the aminal carbon. The aminal can be isolated by silica chromatography as long as ammonia is a component of the eluent: otherwise it decomposes on silica to the amine fragment IIIc. Normally the aminal is not isolated, however, but is directly hydrolyzed to the amine fragment IIIc. This hydrolysis can be accomplished by exposing the aminal to virtually any mild acid in the presence of water. A preferred method of accomplishing this hydrolysis involves exposing the aminal to a mixture of THF, ethanol, and pH 4 aqueous acetic acid at room temperature. The reaction is allowed to proceed for between 5 and 48 hours, with 16 hours preferred.

EXAMPLE 1

Preparation of 11,12,12a,13,14,15-hexanor-9-deoxo-9-hydroxyimino-erythromycin A seco acid methyl ester (Va)

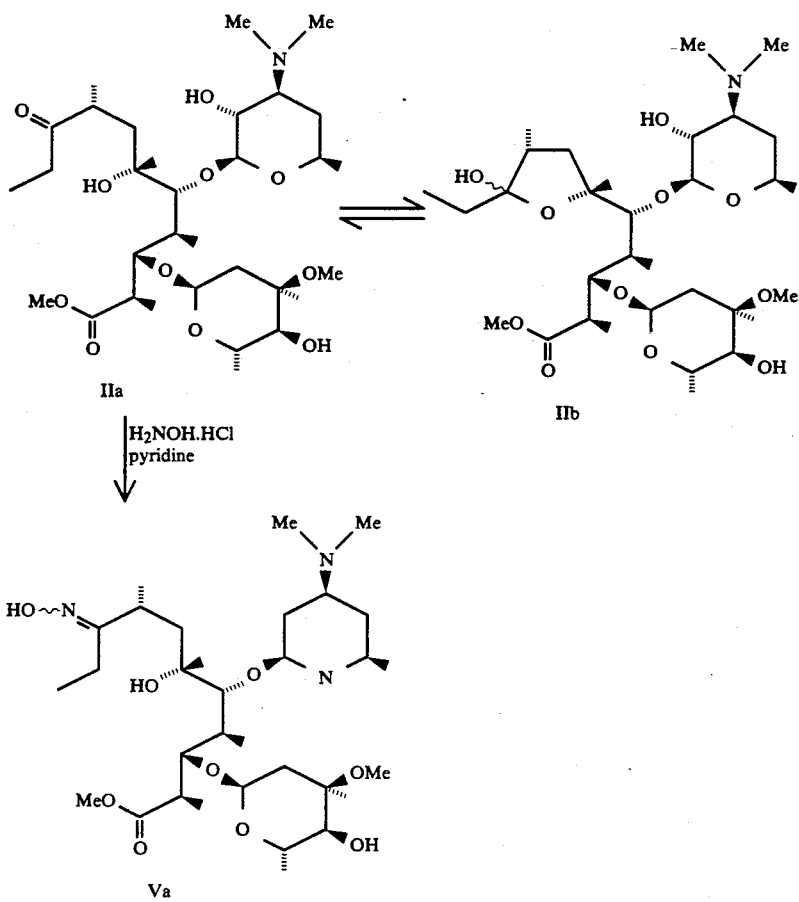

To the 6.0 g of the hemiketal/ketone starting material (IIa/IIb) was added 120 ml pyridine and 3.4 g hydroxylamine hydrochloride, and the mixture was allowed to stir at room temperature for 16 hours. The reaction was then concentrated almost to dryness under reduced pressure, and the residue was partitioned between 500 ml $CH_2Cl_2$ and 200 ml sat. aq. $NaHCO_3$. The aqueous layer was extracted twice with 100 ml $CH_2Cl_2$, and the combined organics were dried over $MgSO_4$ and rotovapped to a foamy solid. This solid was chromatographed on silica eluting with 93:7:1 $CH_2Cl_2$:MeOH:aq. $NH_3$ to yield 4.5 g of pure oxime Va.

There is no obvious doubling of peaks in the proton NMR spectrum, but doubling of some peaks can be seen in the carbon NMR spectrum. From rough integration it seems that the minor oxime isomer (presumably Z) accounts for 10–20% of the product mixture.

Selected spectral data for Va:

$^1$H NMR (400 MHz, $CDCl_3$) δ 4.51 (d, H-1''), 4.27 (d, H-1'), 4.02 (dd, H-3), 3.95 (dq, H-5''), 3.49 (m, H-5'), 3.40 (d, H-5), 3.25 (dd, H-2'), 3.56 (s, $COOCH_3$), 3.17 (s, $OCH_3$), 2.21 (s, $N(CH_3)_2$), 2.80 (dq, H-2), 2.49 (dt, H-3'), 2.19 (d, H-2'' eq), 1.61 (d, H-4'), 1.37 (dd, H-2'' ax)

$^{13}$C NMR of major isomer ($CDCl_3$) δ 176.23, 166.81, 104.46, 96.40, 85.95, 80.31, 77.81, 74.39, 72.75, 70.60, 69.47, 65.43, 64.78, 51.67, 50.20, 49.28, 41.67, 40.37, 37.86, 35.13, 34.33, 29.48, 23.73, 21.44, 20.98, 20.68, 20.21, 17.69, 10.73, 10.64, 10.38

$^{13}$C NMR of minor isomer ($CDCl_3$) δ 176.13, 166.26, 104.57, 86.02, 80.25, 70.48, 69.65, 65.50, 64.68

FAB MS: 655 (M+Li$^+$), 649 (M+H$^+$)

EXAMPLE 2

Preparation of 11,12,12a,13,14,15-hexanor-6-O-methyl-9-deoxo-9-hydroxyimino-erythromycin A seco acid methyl ester as a mixture of C8 epimers (Vb)

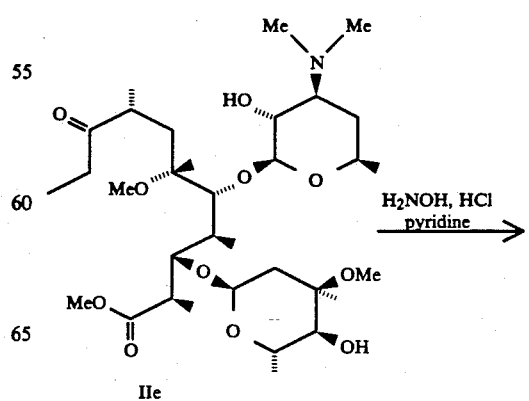

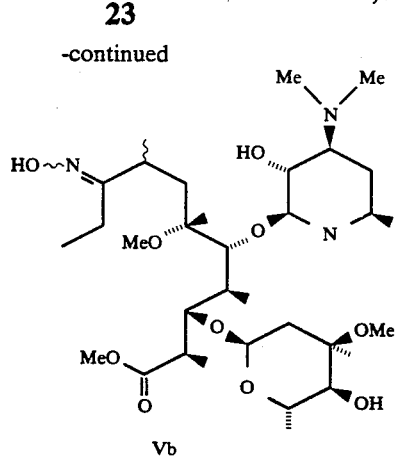

Vb

To the 1.61 g of the ketone starting material IIe was added 30 ml pyridine and 0.9 g hydroxylamine hydrochloride, and the mixture was allowed to stir at room temperature for 16 hours. The reaction was then concentrated almost to dryness under reduced pressure, and the residue was partitioned between 500 ml $CH_2Cl_2$ and 200 ml sat. aq. $NaHCO_3$. The aqueous layer was extracted twice with 100 ml $CH_2Cl_2$, and the combined organics were dried over $MgSO_4$ and evaporated under reduced pressure to give a foamy solid. This solid was chromatographed on silica eluting with 95:5:0.5 $CH_2Cl_2$:MeOH:aq. $NH_3$ to yield 1.6 g of pure oxime Vb.

The product of this reaction is in theory a mixture of four compounds: the 8-R E-oxime, the 8-S E-oxime, the 8-R Z-oxime, and the 8-S Z-oxime. The product mix can be separated into two fractions using careful silica chromatography: one fraction presumably corresponds to the 8-R compounds and the other to the 8-S, but this is unproven.

Selected spectral data for Vb:

$^1H$ NMR of higher $R_f$ fraction (400 MHz, $CDCl_3$) δ 4.62 (d, H-1″), 4.39 (d, H-1′), 3.95 (m, H-5″ and H-3), 3.62 (s, $COOCH_3$), 3.29 (s, 5′-$OCH_3$), 3.05 (s, 6-$OCH_3$), 2.28 (s, $N(CH_3)_2$)

$^1H$ NMR of lower $R_f$ fraction (400 MHz, $CDCl_3$) δ 4.62 (d, H-1″), 4.39 (d, H-1′), 3.95 (m, H-5″ and H-3), 3.60 (s, $COOCH_3$), 3.30 (s, 5′-$OCH_3$), 3.19 (s, 6-$OCH_3$), 2.28 (s, $N(CH_3)_2$)

FAB MS of higher $R_f$ fraction: 670 (M+Li+)
FAB MS of lower $R_f$ fraction: 670 (M+Li+)

EXAMPLE 3

A General Procedure for the Preparation of Oxime Fragments V

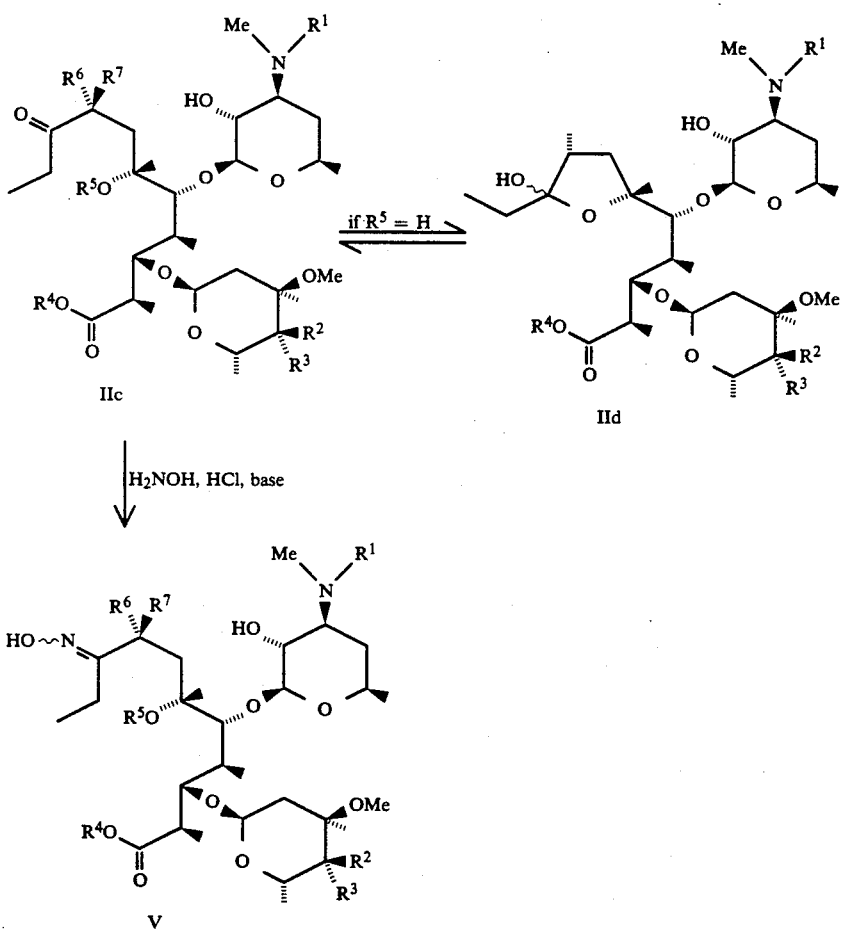

Using the procedure taught in examples 1 and 2, an erythromycin fragment starting material (IIc/IId) is converted into an oxime fragment V, which in general is a mixture of the E and Z forms at the oxime with E predominating. In the above diagram $R^1$ is hydrogen, methyl, $C_{1-10}$ alkoxycarbonyl, aralkoxycarbonyl or arylsulfonyl; one of $R^2$ and $R^3$ is hydrogen, the other is OH, $NHR^1$ or $NMeR^1$ where $R^1$ is as defined before; $R^4$ is hydrogen, $C_{1-10}$ alkyl, or aralkyl; $R^5$ is hydrogen or $C_{1-3}$ alkyl; if $R^5$ is hydrogen, then $R^6$ is methyl and $R^7$ is hydrogen and the two structures for the erythromycin starting material exist in equilibrium with each other; if $R^5$ is alkyl, then one of $R^6$ and $R^7$ is hydrogen and the other is methyl and the erythromycin starting material exists only as the structure on the left. A representative but nonlimiting sampling of the compounds which may be produced in this manner include those in the following table wherein it is understood that the oxime products are species of oxime genus V, the generic structure of which is given above.

TABLE FOR EXAMPLE 3

|  |  | \multicolumn{7}{c}{Substituent} |
|---|---|---|---|---|---|---|---|---|
|  |  | $R^1$ | $R^2$ | $R^3$ | $R^4$ | $R^5$ | $R^6$ | $R^7$ |
| Oxime | V1 | Me | H | $NH_2$ | Me | H | Me | H |
| Products | V2 | Me | $NH_2$ | H | Me | H | Me | H |
|  | V3 | Me | OH | H | Me | n-Pr | Me | H |
|  | V4 | Me | OH | H | H | Me | Me | H |
|  | V5 | $PhSO_2$ | OH | H | Me | Me | Me | H |
|  | V6 | Me | OH | H | Bn | Me | Me | H |
|  | V7 | t-BOC | OH | H | Me | Me | Me | H |
|  | V8 | Cbz | OH | H | Me | Me | Me | H |

Ph = phenyl
t-BOC = t-butyloxycarbonyl
Cbz = benzyloxycarbonyl
n-Pr = n-propyl
Bn = benzyl

EXAMPLE 4

Preparation of 11,12,12a,13,14,15-hexanor-9-deoxo-9-amino-erythromycin A seco acid methyl ester as a mixture of C-9 epimers (IVa)

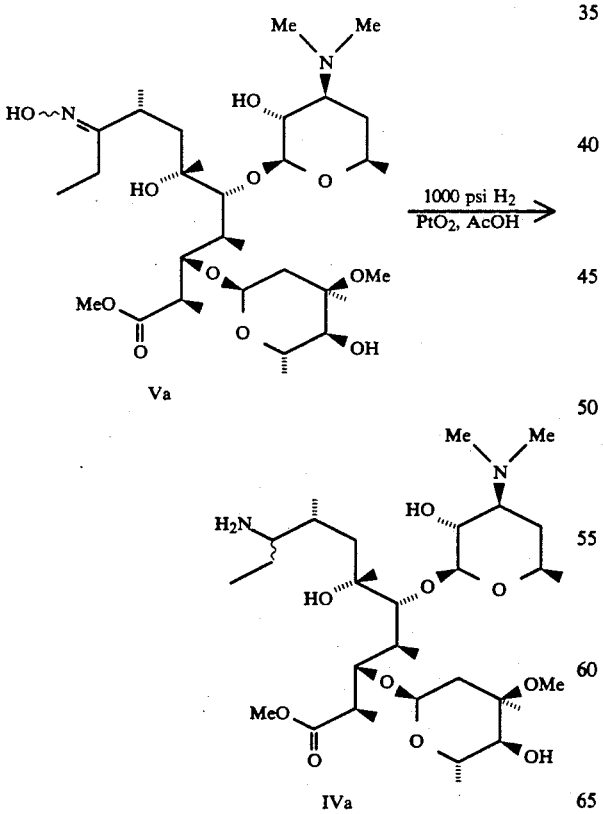

A hydrogenation vessel was charged with 3.7 g of the oxime starting material (Va), along with 60 ml of AcOH and 3.7 g of $PtO_2$. This was subjected to 1000 psi of $H_2$ for 24 hours. The solution was then filtered carefully through a medium glass frit under an inert atmosphere (to prevent ignition of the platinum) and the platinum was washed three times with AcOH. The AcOH was removed under vacuum, and the residue was partitioned between 300 ml $CH_2Cl_2$ and 100 ml sat. aq. $NaHCO_3$. The aqueous layer was washed twice with 50 ml $CH_2Cl_2$ and the combined organics were dried over $MgSO_4$ and rotovapped to a foamy solid. This solid was chromatograped on silica, eluting with 88:12:1 $CH_2Cl_2$:MeOH:aq. $NH_3$ to yield 2.85 g of pure amine IVa, as an approximately 1:1 mixture of diasteromers at C9. Peak doublings are mostly not seen in the proton NMR, but may be seen in the carbon NMR.

Selected spectral data:

$^1H$ NMR of diastereomeric mixture (400 MHz, $CDCl_3$) δ 4.61 (d, H-1''), 4.36 (d, H-1'), 4.11 (dd, H-3), 4.02 (dq, H-5''), 3.62 (s, $COOCH_3$), 3.55 (m, H-5'), 3.50 (d, H-5), 3.30 (dd, H-2'), 3.25 (s, $OCH_3$), 3.95 (d, H-4''), 2.81 (m, H-2), 2.50 (dt, H-3'), 2.28 (s, $N(CH_3)_2$), 2.26 (m, H-2'), 2.05 (m, H-4')

$^{13}C$ NMR of diastereomeric mixture ($CDCl_3$) δ 176.31, 104.63, 104.50, 96.17, 96.08, 86.56, 86.25, 80.29, 77.85, 74.22, 73.78, 72.73, 70.52, 70.44, 69.56, 65.38, 65.11, 51.65, 49.31, 42.67, 40.35, 37.65, 37.56, 35.13, 28.92, 24.25, 23.92, 21.55, 21.12, 17.75, 10.97, 10.41

FAB MS: 635 (M+H+)

EXAMPLE 5

Preparation of 11,12,12a,13,14,15-hexanor-6-O-methyl-9-deoxo-9-amino-erythromycin A seco acid methyl ester as a mixture of C-8 and C-9 epimers (IVb)

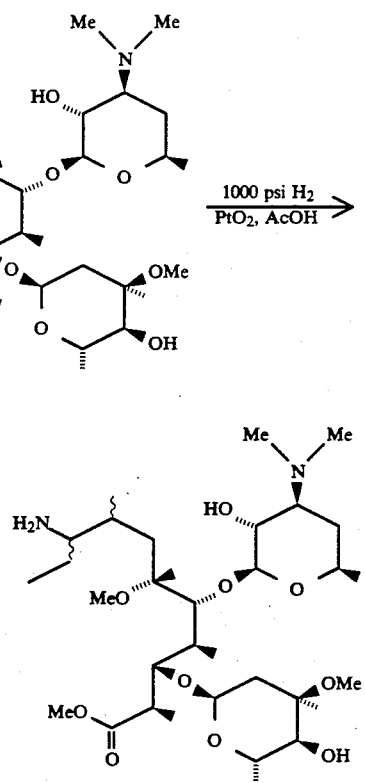

A hydrogenation vessel was charged with 1.6 g of the oxime Vb along with 15 ml of AcOH and 1.7 g of PtO₂. This was subjected to 1000 psi of H₂ for 48 hours. The solution was then filtered carefully through a medium glass frit under an inert atmosphere (to prevent ignition of the platinum) and the platinum was washed three times with AcOH. The AcOH was removed under vacuum, and the residue was partitioned between 300 ml CH₂Cl₂ and 100 ml sat. aq. NaHCO₃. The aqueous layer was washed twice with 50 ml CH₂Cl₂ and the combined organics were dried over MgSO₄ and rotovapped to a foamy solid. This solid was chromatograped on silica, eluting with 90:10:1 CH₂Cl₂:MeOH:aq. NH₃ to yield 1.27 g of pure amine mixture IVb. Rough integration of the quadrupled resonance around δ 95 in the carbon NMR indicates that the product mixture is composed of approximately equal amounts of the four possible diastereomers.

Selected spectral data:

¹H NMR of four component diastereomeric mixture (400 MHz, CDCl₃) δ 4.63 (m, H-1″), 4.40 (m, H-1′), 3.98 (m, H-3 & H-5″), 3.65 (d, H-5), 3.61 (s, COOCH₃), 3.45 (m, H-5′), 3.25 (s, 3″—OCH₃), 3.15 (s, 6-OCH₃), 2.94 (d, H-4″), 2.23 (s, N(CH₃)₂), 2.26 (m, H-2′), 1.61 (d, H-4′)

¹³C NMR of four component diastereomeric mixture (CDCl₃) δ 176.19, 176.11, 102.71, 102.48, 102.42, 95.16, 95.07, 94.99, 94.92, 79.97, 79.89, 79.76, 79.73, 79.39, 79.32, 79.19, 78.85, 77.98, 72.73, 70.88, 70.81, 68.92, 65.27, 58.34, 51.62, 51.59, 50.23, 50.12, 49.98, 49.33, 41.62, 41.42, 41.39, 40.36, 37.77, 37.60, 37.37, 36.87, 36.78, 36.36, 35.09, 33.00, 29.03, 28.94, 28.82, 27.61, 27.19, 21.58, 21.24, 21.04, 20.97, 20.83, 20.47, 18.03, 17.63, 16.88, 14.79, 14.74, 14.12, 11.44, 11.40, 11.21, 11.14, 10.96, 10.89, 10.83, 10.79, 10.67

FAB MS: 656 (M+Li+)

EXAMPLE 6

A General Procedure for the Preparation of 9a-Aza Fragments IV

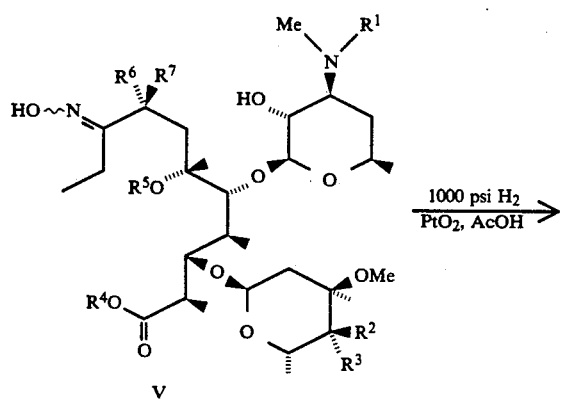

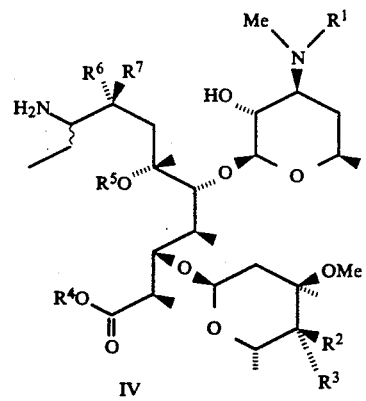

Using the procedure taught in examples 4 and 5, an oxime fragment V is converted into a 9a-aza fragment IV, which in general is a mixture of the R and S forms at C9. In the above diagram R¹ is hydrogen, methyl, C₁₋₁₀ alkoxycarbonyl, aralkoxycarbonyl or arylsulfonyl; one of R² and R³ is hydrogen, the other is OH, NHR¹ or NMeR¹ where R¹ is as defined before; R⁵ is hydrogen or C₁₋₃ alkyl; if R⁵ is hydrogen, then R⁶ is methyl and R⁷ is hydrogen; if R⁵ is alkyl, then one of R⁶ and R⁷ is hydrogen and the other is methyl; R⁴ is hydrogen, C₁₋₁₀ alkyl, or aralkyl.

A representative but nonlimiting sampling of the compounds which may be produced in this manner include those in the following tables wherein it is to be understood that the starting materials are species of the oxime genus V and the products are species of the 9a-aza genus IV, whose generic structures are given above.

TABLE FOR EXAMPLE 6

|  |  | Substituent | | | | | | |
| --- | --- | --- | --- | --- | --- | --- | --- | --- |
|  |  | R¹ | R² | R³ | R⁴ | R⁵ | R⁶ | R⁷ |
| Amine | IV1 | Me | H | NH₂ | Me | H | Me | H |
| Product | IV2 | Me | NH₂ | H | Me | H | Me | H |
| Compounds | IV3 | Me | OH | H | Me | n-Pr | Me | H |
|  | IV4 | Me | OH | H | H | Me | Me | H |
|  | IV5 | PhSO₂ | OH | H | Me | Me | Me | H |
|  | IV6 | t-BOC | OH | H | Me | Me | Me | H |
|  | IV7 | Cbz | OH | H | Me | Me | Me | H |

Ph = phenyl
t-BOC = t-butyloxycarbonyl
Cbz = benzyloxycarbonyl
n-Pr = n-propyl
Bn = benzyl

EXAMPLE 7

Preparation of 11,12,12a,13,14,15-hexanor-8a-aza-9-deoxo-8a,9-didehydro-6,9-epoxyerythromycin A seco acid methyl ester, 11,12,12a,13,14,15-hexanor-8a-aza-9-deoxo-18a,9-didehydro-6,9-epoxy-8-epierythromycin A seco acid methyl ester, 10,10a,11,12,12a,13,14,15-octanor-6,9-epoxyerythromycin A seco acid methyl ester, and 10,10a,11,12,12a,13,14,15-octanor-6,9-epoxy-8-epierythromycin A seco acid methyl ester

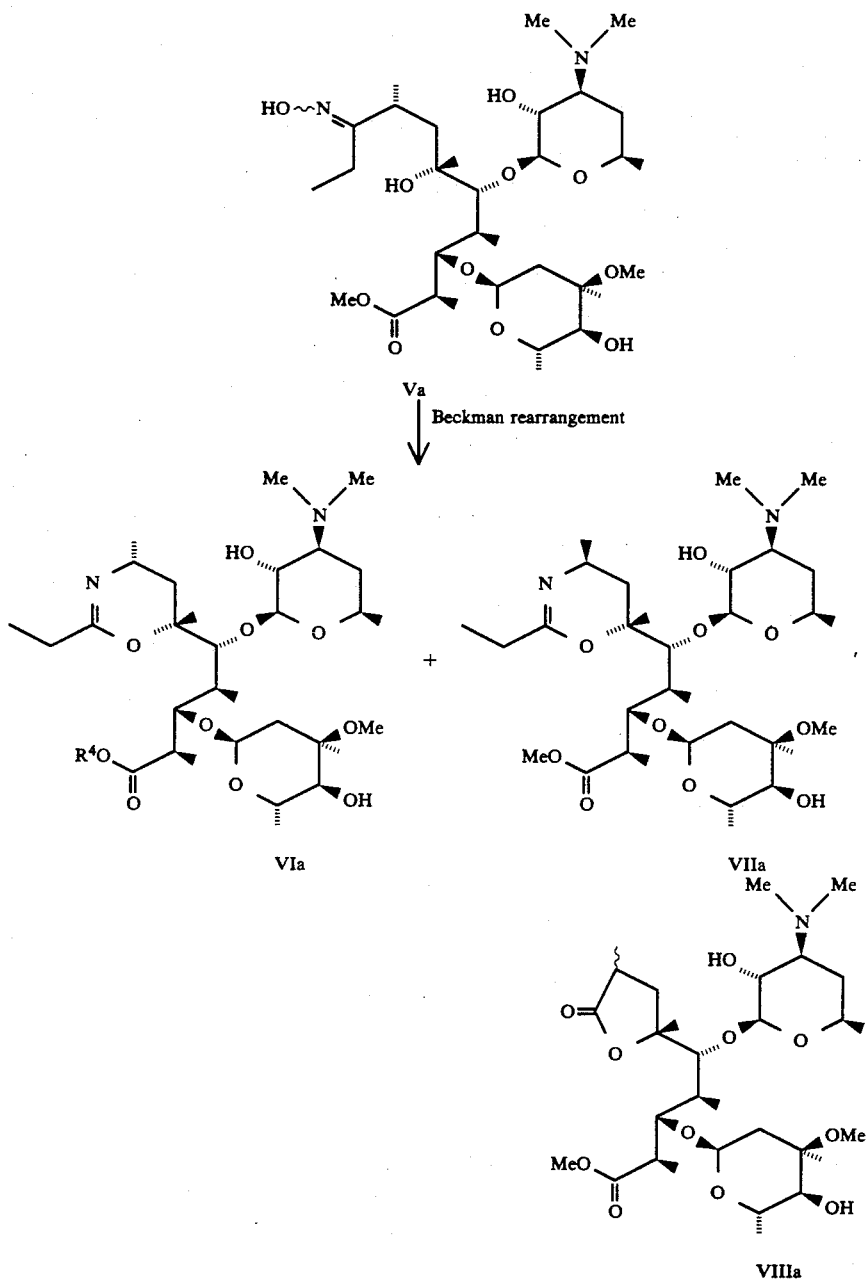

Method 1:

To a 50 ml flask was introduced 5.45 g of oxime Va and 1.5 g of tosyl chloride, and 5 ml of dry pyridine. The reaction was stirred at room temperature for 18 hours. Approximately 100 ml of methylene chloride was added to the reaction, and the organic layer was extracted twice with 0.1M NaOH. The organic layer was separated, dried over MgSO₄, and the solvent was removed under reduced pressure. The resulting residue was chromatographed on silica eluting with 94:6:1 CH₂Cl₂:MeOH:aq. NH₃ to yield 3.06 g of product VIa (contaminated with approximately 5% of lactone by-product VIIIa, which does not interfere in subsequent reactions), and 1.72 g of a mixture of product VIa, 8-epimeric product VIIa, and starting material. If desired, a second careful chromatography can provide pure samples of VIa, VIIa and VIIIa: In the 94:6:1 CH₂Cl₂:MeOH:aq. NH₃ solvent system the lactones VIIIa elute first followed closely by the desired iminoether VIa and it is difficult to separate the two. Next eluting but relatively easy to separate from the higher $R_f$ compounds is the epi-iminoether VIIa, followed closely by unreacted starting material.

Selected spectral data for 11,12,12a,13,14,15-hexano-8a-aza-9-deoxo-8a,9-didehydro-6,9-epoxyerythromycin A seco acid methyl ester VIa:

¹H NMR (400 MHz, CDCl₃) δ 4.61 (d, H-1″), 4.41 (d, H-1′), 4.09 (dd, H-3), 3.99 (dq, H-5″), 3.72 (d, H-5), 3.64 (s, COOCH₃), 3.49 (m, H-5′), 3.34 (m, H-8), 3.26 (s, OCH₃), 3.21 (m, H-2′), 2.95 (d, H-4″), 2.78 (m, H-2), 2.48 (d, H-3′), 2.25 (s, N(CH₃)₂), 2.25 (m, H-2″), 2.11 (q, H-10), 2.01 (dt, H-4), 1.80 (d, H-7), 1.65 (d, H-4′), 1.45 (dd, H-2″ ax), 1.32 (s, 6-Me), 1.28 (d, H-7), 1.18 (d, H-4′), 1.08 (d, 2-Me+4-Me), 1.05 (t, H-11), $^{13}$C NMR (CDCl$_3$) δ 176.29, 159.76, 103.02, 95.48, 80.35, 80.00, 78.84, 77.97, 72.75, 70.62, 69.46, 65.57, 65.44, 65.28, 51.75, 49.37, 44.56, 41.29, 40.34, 36.77, 35.14, 33.72, 28.90, 28.75, 24.14, 23.26, 21.62, 21.20, 17.94, 11.38, 10.94, 10.29

FAB MS: 637 (M+Li$^+$)

Selected spectral data for 11,12,12a,13,14,15-hexanor-8a-aza-9-deoxo-8a,9-didehydro-6,9-epoxy-8-epierythromycin A seco acid methyl ester VIIa:

$^1$H NMR (400 MHz, CDCL$_3$) δ 4.59 (d, H-1''), 4.39 (d, H-1'), 4.02 (dd, H-3), 3.92 (dq, H-5''), 3.71 (d, H-5), 3.63 (s, COOCH$_3$), 3.45 (m, H-5'), 3.45 (m, H-8), 3.27 (m, H-2'), 3.24 (s, OCH$_3$), 2.93 (d, H-4''), 2.70 (m, H-2), 2.45 (d, H-3'), 2.25 (s, N(CH$_3$)$_2$), 2.25 (m, H-2''), 2.18 (q, H-10), 2.12 (d, H-7), 1.92 (dt, H-4), 1.63 (d, H-4'), 1.45 (dd, H-2'' ax), 1.30 (s, 6-Me), 1.18 (dd, H-4'), 1.15 (d, H-7), 1.06 (d, 2-Me+4-Me), 1.06 (t, H-11),

FAB MS: 637 (M+Li$^+$)

Selected spectral data for the mixture of 10,10a,11,12,12a,13,14,15-octanor-6,9-epoxyerythromycin A seco acid methyl ester and 10,10a,11,12,-12a,13,14,15-octanor-6,9-epoxy-8-epierythromycin A secon acid methyl ester VIIIa:

$^1$H NMR (400 MHz, CDCL$_3$) δ 4.71 and 4.65 (d, H-1''), 4.45 and 4.41 (d, H-1'), 4.02 (m, H-3), 3.95 (dq, H-5''), 3.64 and 3.62 (s, COOCH$_3$), 3.49 (m, H-8), 3.26 (s, OCH$_3$), 3.15 (dd, H-2'), 2.95 (d, H-4''), 2.71 (m, H-2), 2.45 (d, H-3'), 2.27 (s, N(CH$_3$)$_2$), 1.66 (d, H-4'), 1.45 (dd, H-2'' ax), 1.30 (s, 6-Me), 1.18 (dd, H-4'), 1.15 (d, H-7), 1.06 (d, 2-Me+4-Me), 1.06 (t, H-11),

FAB MS: 605 (M+H$^+$)

IR: 1762, 1730, 1665 cm$^{-1}$

EXAMPLE 8

A General Procedure for the Preparation of Iminoethers VI and VII

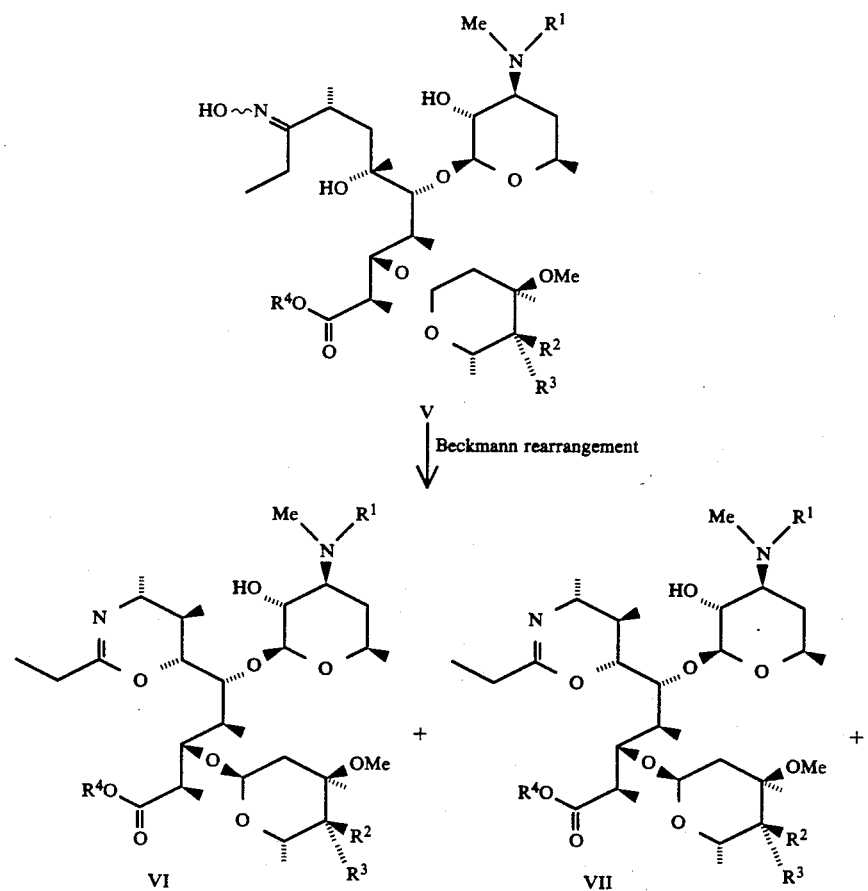

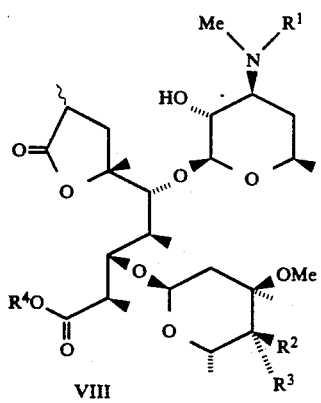

VIII

Using the procedure taught in example 7, an oxime fragment V is converted into a mixture of iminoethers VI and VII and lactones VIII, with the iminoether VI being the major product of the reaction. In the above diagram $R^1$ is hydrogen, methyl, $C_{1-10}$ alkoxycarbonyl, aralkoxycarbonyl or arylsulfonyl; one of $R^2$ and $R^3$ is hydrogen, the other is OH, $NHR^1$ or $NMeR^1$ where $R^1$ is as defined before; $R^4$ is hydrogen, $C_{1-10}$ alkyl, or aralkyl.

A representative but nonlimiting sampling of the compounds which may be produced in this manner include those in the following table where it is to be understood that the starting oxime compounds are species of the oxime genus V and the desired products are iminoethers of the genera VI and VII, whose generic structure is given above.

TABLE FOR EXAMPLE 8

| | | Substituent | | | |
|---|---|---|---|---|---|
| | | $R^1$ | $R^2$ | $R^3$ | $R^4$ |
| Imino- | VI-1, VII-1 | Me | H | $NH_2$ | Me |

| | | Substituent | | | |
|---|---|---|---|---|---|
| | | $R^1$ | $R^2$ | $R^3$ | $R^4$ |
| ether Products | VI-2, VII-2 | Me | $NH_2$ | H | Me |
| | VI-3, VII-3 | Me | OH | H | Me |
| | VI-4, VII-4 | Me | OH | H | H |
| | VI-5, VII-5 | $PhSO_2$ | OH | H | Me |
| | VI-6, VII-6 | Me | OH | H | Bn |
| | VI-7, VII-7 | t-BOC | OH | H | Me |
| | VI-8, VII-8 | Cbz | OH | H | Me |

Ph = phenyl
t-BOC = t-butyloxycarbonyl
Cbz = benzyloxycarbonyl
n-Pr = n-propyl
Bn = benzyl

EXAMPLE 9

Preparation of 11,12,12a,13,14,15-hexanor-8a-aza-9-deoxo-6,9-epoxyerythromycin A seco acid methyl ester (single diastereomer of uncertain configuration at C-9) (IXa) and 9,10,10a,11,12,12a,13,14,15-nonanor-8a-aza-erythromycin A seco acid methyl ester (IIIa)

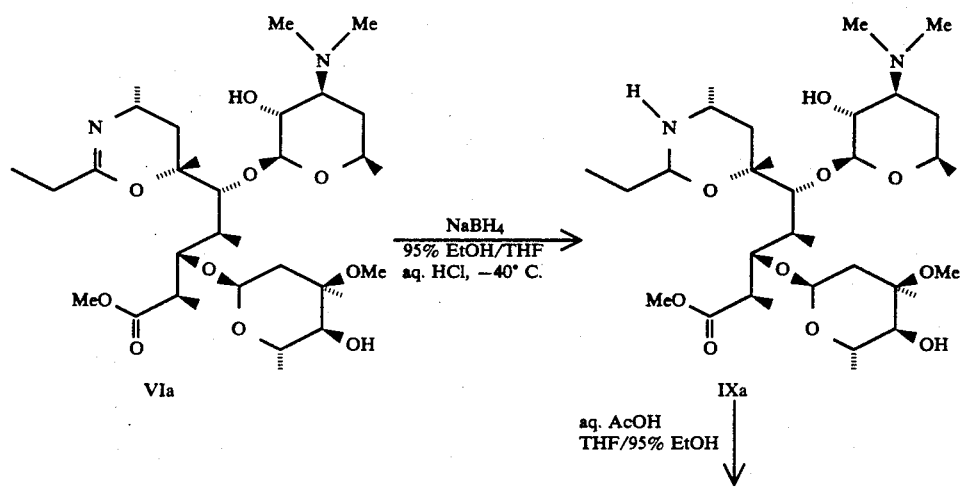

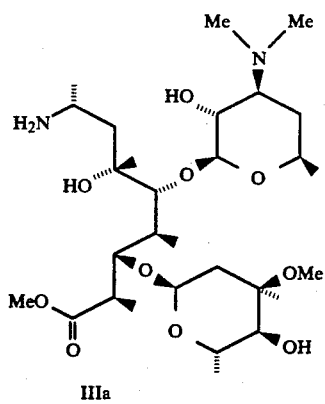

IIIa

To a 2 l flask was introduced 1.94 g of iminoether starting material VIa (contaminated with approximately 5% lactones (VIIIa, see example 7) and 500 ml of 1:1 95% EtOH:THF. The reaction was stirred and cooled to −40° C. A solution of 360 mg NaBH$_4$ in 3 ml H$_2$O was prepared and added dropwise to the stirred, chilled reaction. The "pH" of the solution was checked by applying a drop of the solution to wet pH paper, and the initial "pH" was 9 to 10. At this point, 8.1 ml of 2N HCl was added, after which the "pH" was approximately 7. The reaction was allowed to stir at −40° to −45° C. for 16 hours, at which time about two-thirds of the solvent was removed under reduced pressure without warming above 10° C. Normally the aminal IXa was not isolated, but was hydrolyzed directly to the amine IIIa. About 800 ml of water was added to the solution, and the pH was adjusted to 4 using AcOH and monitoring with a pH meter. The solution was stirred at room temperature for 16 to 24 hours, and then basified to pH 14 with 5N NaOH. The aqueous solution was extracted four times with 200 ml of methylene chloride, and this organic solution was dried over MgSO$_4$ and rotovapped. The crude white foam was chromatographed on silica eluting with 90:10:1 CH$_2$Cl$_2$:MeOH:aq. NH$_3$ to yield 567 mg of higher R$_f$ material (lactone impurity in the starting material plus some aminal), and 1.25 g of pure amine IIIa.

Selected spectral data for 11,12,12a,13,14,15-hexanor-8a-aza-9-deoxo-6,9-epoxyerythromycin A seco acid methyl ester (single diastereomer of uncertain configuration at C-9)(IXa):

$^1$H NMR (400 MHz, CDCL$_3$) δ 4.61 (d, H-1″), 4.40 (d, H-1′), 4.22 (dd, H-9), 4.12 (dd, H-3), 4.01 (dq, H-5″), 3.58 (d, H-5), 3.63 (s, COOCH$_3$), 3.50 (m, H-5′), 3.27 (s, OCH$_3$), 3.21 (m, H-2′), 2.99 (d, H-4″), 2.82 (m, H-2), 2.47 (d, H-3′), 2.25 (s, N(CH$_3$)$_2$), 2.25 (m, H-2″), 1.64 (d, H-4′), 0.87 (t, H-11), $^{13}$C NMR (CDCL$_3$) δ 176.74, 102.89, 95.13, 82.25, 81.18, 80.31, 78.05, 77.39, 70.69, 69.32, 65.56, 65.12, 51.59, 49.39, 45.66, 40.85, 40.33, 38.99, 37.50, 36.02, 35.18, 29.34, 28.85, 22.85, 21.63, 21.18, 20.87, 17.91, 11.66, 10.20, 9.71

FAB MS: 639 (M+Li+)

Selected spectral data for 9,10,10a,11,12,12a,13,14,15-nonanor-8a-azaerythromycin A seco acid methyl ester (IIIa):

$^1$H NMR (400 MHz, CDCL$_3$) δ 4.60 (d, H-1″), 4.33 (d, H-1′), 4.10 (dd, H-3), 4.00 (dq, H-5″), 3.63 (s, COOCH$_3$), 3.53 (m, H-5′), 3.48 (d, H-5), 3.28 (dd, H-2′), 3.25 (s, OCH$_3$), 3.25 (m, H-8), 2.95 (d, H-4″), 2.79 (dq, H-2), 2.49 (m, H-3′), 2.27 (s, N(CH$_3$)$_2$), 2.26 (dd, H-2″), 2.04 (m, H-4), 2.49 (dt, H-3′), 1.64 (br d, H-4′), 1.45 (dd, H-2″ax), 1.45 (m, H-7), 1.35 (m, H-7), 1.24 (s, H-6Me), 1.21 (m, H-6′ or 6″), 1.21 (m, H-4′), 1.20 (s, H-6′ or 6″), 1.16 (s, H-3″Me), 1.09 (d, H-2Me), 1.09 (d, H-8Me), 1.04 (d, H-4Me).

$^{13}$C NMR (CDCL$_3$) δ 176.35 (C-1), 104.37 (C-1′), 95.98 (C-1″), 85.70 (C-5), 80.33 (C-3), 77.79 (C-4″), 75.01 (C-6), 72.66 (C-3″), 70.39 (C-2′), 69.57 (C-5′), 65.30 (C-5″), 65.11 (C-3′), 51.65 (C-ester Me), 49.34 (C-3″—OMe), 44.16 (C-7), 43.96 (C-8), 41.24 (C-2), 35.11 (C-2″), 28.81 (C-4′), 26.51 (C-8Me or 2Me), 24.39 (C-6Me), 21.50 (C-3″Me), 21.05 (C-6′), 17.73 (C-6″), 11.00 (C-4Me), 10.08 (C-8Me or 2Me).

FAB MS: 594 (M+H+)

EXAMPLE 10

A General Procedure for the Preparation of Aminals IX and X and 8a-Aza Fragments IIIc and IIId

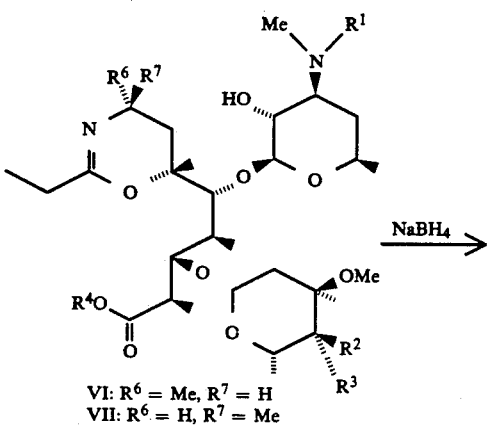

VI: R$^6$ = Me, R$^7$ = H
VII: R$^6$ = H, R$^7$ = Me

-continued

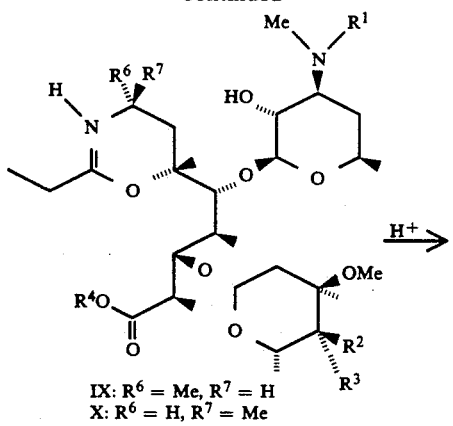

IX: R⁶ = Me, R⁷ = H
X: R⁶ = H, R⁷ = Me

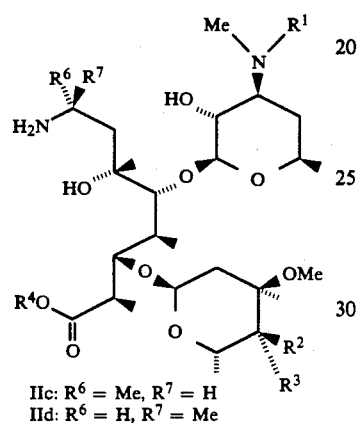

IIc: R⁶ = Me, R⁷ = H
IId: R⁶ = H, R⁷ = Me

Using the procedure taught in example 9, an iminoether fragment VI or VII is converted into an aminal IX or X, respectively, which is hydrolyzed to an 8a-aza fragment IIIc or IIId, respectively. In the above diagram $R^1$ is hydrogen, methyl, $C_{1-10}$ alkoxycarbonyl, aralkoxycarbonyl or arylsulfonyl; one of $R^2$ and $R^3$ is hydrogen, the other is OH, $NHR^1$ or $NMeR^1$ where $R^1$ is as defined before; $R^4$ is hydrogen, $C_{1-10}$ alkyl, or aralkyl. A representative but nonlimiting sampling of the compounds which may be produced in this manner include those in the following table wherein it is to be understood that the product compounds are species of the genus of 8a-aza fragments IIIc or IIId, whose generic structure is given above.

TABLE FOR EXAMPLE 10

|  |  | Substituent |  |  |  |  |  |
|---|---|---|---|---|---|---|---|
|  |  | R¹ | R² | R³ | R⁴ | R⁶ | R⁷ |
| Product | III-1 | Me | OH | H | Me | H | Me |
| Compound | III-2 | Me | H | NH₂ | Me | Me | H |
|  | III-3 | Me | NH₂ | H | Me | Me | H |
|  | III-4 | Me | OH | H | Me | Me | H |
|  | III-5 | Me | OH | H | H | Me | H |
|  | III-6 | PhSO₂ | OH | H | Me | Me | H |
|  | III-7 | Me | OH | H | Bn | Me | H |
|  | III-8 | t-BOC | OH | H | Me | Me | H |
|  | III-9 | Cbz | OH | H | Me | Me | H |
|  | III-10 | Me | H | NH₂ | Me | H | Me |
|  | III-11 | Me | NH₂ | H | Me | H | Me |
|  | III-12 | Me | OH | H | Me | H | Me |
|  | III-13 | Me | OH | H | H | H | Me |
|  | III-14 | PhSO₂ | OH | H | Me | H | Me |
|  | III-15 | Me | OH | H | Bn | H | Me |
|  | III-16 | t-BOC | OH | H | Me | H | Me |

-continued

|  | Substituent |  |  |  |  |  |
|---|---|---|---|---|---|---|
|  | R¹ | R² | R³ | R⁴ | R⁶ | R⁷ |
| III-17 | Cbz | OH | H | Me | Me | H |

Cbz = benzyloxycarbonyl
t-BOC = tert-butyloxycarbonyl
Ph = phenyl
Bn = benzyl

While the invention has been described, exemplified and illustrated in reference to certain preferred embodiments thereof, those skilled in the art will appreciate that various changes, modifications and substitutions can be made therein without departing from the spirit and scope of the invention. It is intended, therefore, that the invention be limited only by the scope of the claims which follow and that such claims be interpreted as broadly as possible.

What is claimed is:

1. A method of synthesizing amine product compounds of the formula

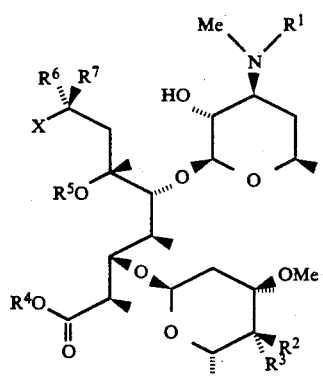

wherein
X is

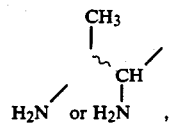

$R^1$ is hydrogen, methyl, $C_{1-10}$ alkoxycarbonyl or arylsulfonyl when X is $CH_3CH_2CHNH_2$ and is additionally aralkoxycarbonyl when X is $NH_2$;

one of $R^2$ and $R^3$ is hydrogen and the other is OH, $NHR^1$ or $NMeR^1$ where $R^1$ is an defined above;

$R^4$ is hydrogen or $C_{1-10}$ alkyl when X is $CH_3CH_2CHNH_2$ and is additionally aralkyl when X is $NH_2$;

$R^5$ is hydrogen or $C_{1-3}$ alkyl when X is $CH_3CH_2CHNH_2$;

$R^5$ is hydrogen when X is $NH_2$;

one of $R^6$ and $R^7$ is hydrogen and the other is methyl except when X is $CH_3CH_2CHNH_2$ and $R^5$ is hydrogen, in which case $R^6$ is methyl and $R^7$ is hydrogen;

said method comprising the steps of
(1) cleaving an erythromycin-like compound of the formula

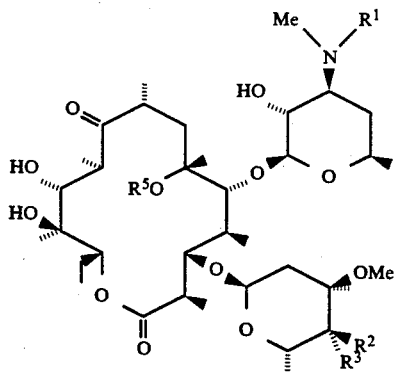

where $R^1$, $R^2$, $R^3$ are as defined before for when X is $NH_2$ and $R^5$ is hydrogen or $C_{1-3}$ alkyl, to produce compounds of the formulae

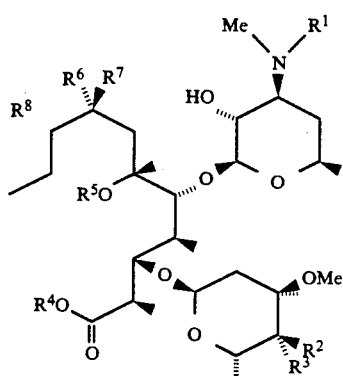

where $R^1$, $R^2$, $R^3$ and $R^4$ are as defined above for when X is $NH_2$, $R^5$ is hydrogen or $C_{1-3}$ alkyl when $R^8$ is oxo, $R^5$ is a covalent bond to the C-9 carbon atom when $R^8$ is hydroxyl, $R^6$ is methyl and $R^7$ is hydrogen when $R^5$ is hydrogen, one of $R^6$ and $R^7$ is methyl and the other is hydrogen when $R^5$ is $C_{1-3}$ alkyl, $R^8$ is oxo when $R^5$ is hydrogen or alkyl and $R^8$ is hydroxyl of either stereochemical orientation when $R^5$ is a covalent bond to the C-9 carbon atom;

(2) converting the product of step (1) into an oxime of the formula

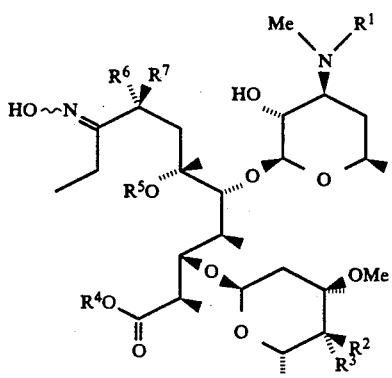

where $R^1$, $R^2$, $R^3$, $R^4$, $R^5$, $R^6$ and $R^7$ are as defined above; and (3) elaborating the oxime product of step (2) to said amine product compound, which is as defined above.

2. A method of synthesizing amine product compounds of the formula

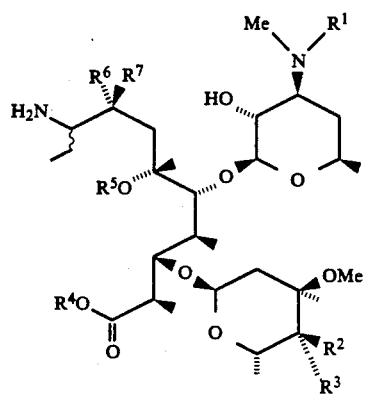

wherein $R^1$ is hydrogen, methyl, $C_{1-10}$ alkoxycarbonyl or phenylsulfonyl;

one of $R^2$ and $R^3$ is hydrogen and the other is NHR, NMeR or OR where R is hydrogen, methyl C1-10 alkoxycarbonyl or phenylsulfonyl;

$R^4$ is hydrogen or $C_{1-10}$ alkyl $R^5$ is hydrogen or $C_{1-3}$ alkyl one of $R^6$ and $R^7$ is hydrogen and the other is methyl when $R^5$ is $C_{1-3}$ alkyl $R^6$ is methyl and $R^7$ is hydrogen when $R^5$ is hydrogen;

said method comprising the steps of (1) cleaving an erythromycin-like compound of the formula

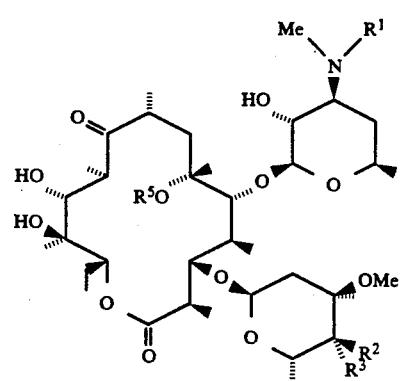

where $R^1$, $R^2$, $R^3$ and $R^5$ are as defined before, to produce compounds of the formula

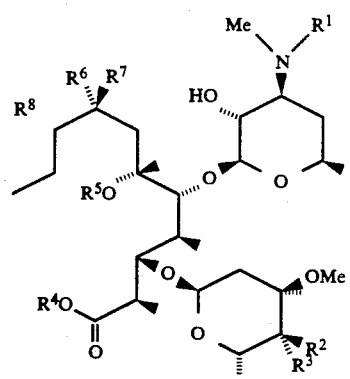

where $R^1$, $R^2$, $R^3$, $R^4$, $R^6$ and $R^7$ are as defined above, $R^5$ is hydrogen or $C_{1-3}$ alkyl when $R^8$ is oxo, $R^5$ is a covalent bond to the C-9 carbon atom when $R^8$ is hydroxyl, $R^8$ is oxo when $R^5$ is hydrogen or alkyl and $R^8$ is hydroxyl of either stereochemical orientation when $R^5$ is a covalent bond to the C-9 carbon atom;

(2) converting the product of step (1) into an oxime of the formula

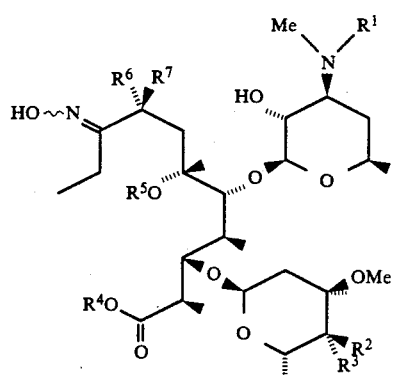

where $R^1$, $R^2$, $R^3$, $R^4$, $R^5$, $R^6$ and $R^7$ are as defined above; and (3) reducing the oxime product of step (2) to said amine product compound, which is as defined above.

3. A method of synthesizing amine product compounds of the formula

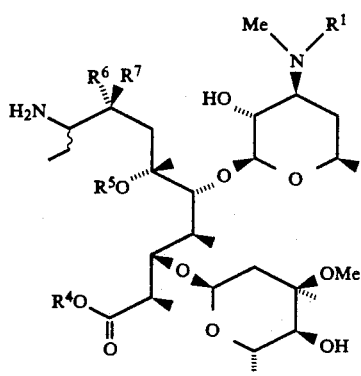

wherein
$R^5$ is hydrogen or methyl;

one of $R^6$ and $R^7$ is hydrogen and the other is methyl when $R^5$ is methyl;
$R^6$ is methyl and $R^7$ is hydrogen when $R^5$ is hydrogen;
said method comprising the steps of
(1) cleaving an erythromycin-like compound of the formula

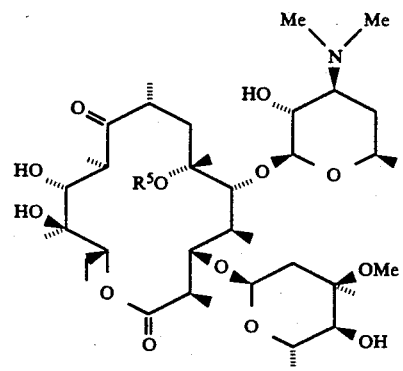

where $R^5$ is as defined before, to produce compounds of the formula

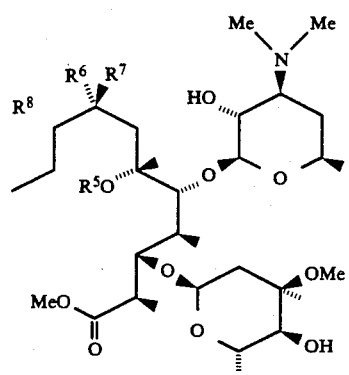

where $R^6$ and $R^7$ are as defined above, $R^5$ is hydrogen or methyl when $R^8$ is oxo, $R^5$ is a covalent bond to the C-9 carbon atom when $R^8$ is hydroxyl, $R^8$ is oxo when $R^5$ is hydrogen or methyl and $R^8$ is hydroxyl of either sterochemical orientation when $R^5$ is a covalent bond to the C-9 carbon atom;

(2) converting the product of step (1) into an oxime of the formula

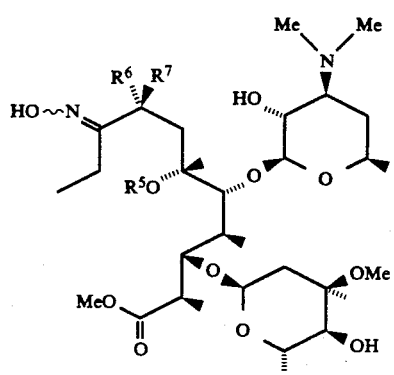

where $R^5$ is hydrogen or methyl and $R^6$ and $R^7$ are as defined above and (3) reducing the oxime product of step (2) to said amine product compound, which is as defined above.

4. A method of synthesizing amine product compounds of the formulae IIIe and IIIf

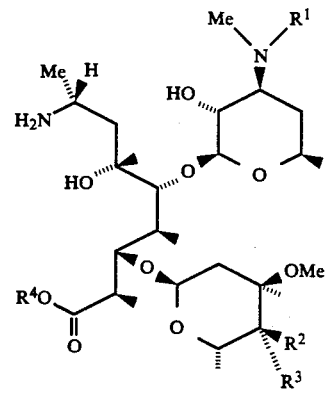

IIIe

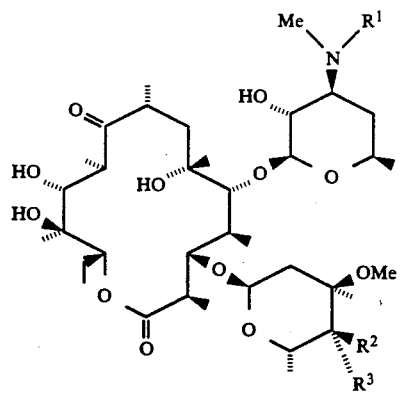

where $R^1$, $R^2$ and $R^3$ are as defined above, to produce compounds of the formulae IIe and IIf

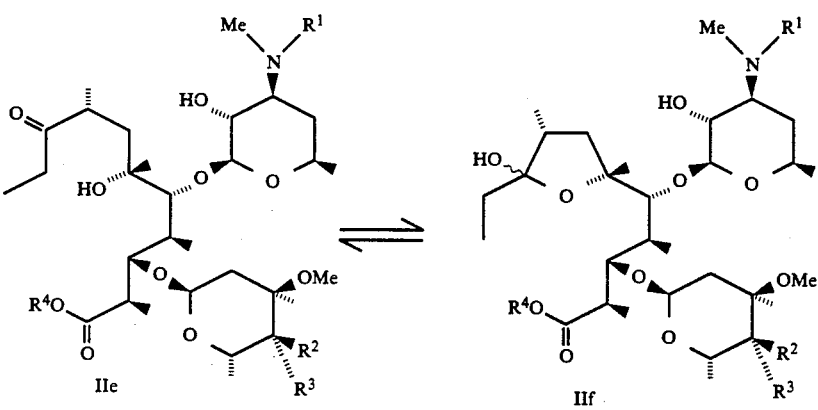

IIe     IIf

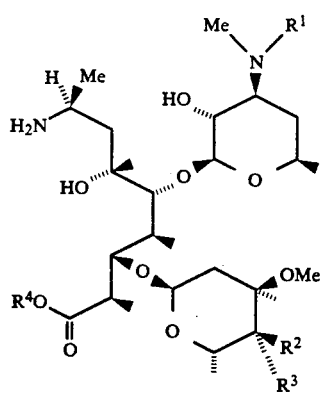

IIIf where $R^1$, $R^2$, $R^3$ and $R^4$ are as defined above, (2) converting the products of step (1) into an oxime of the formula Ve

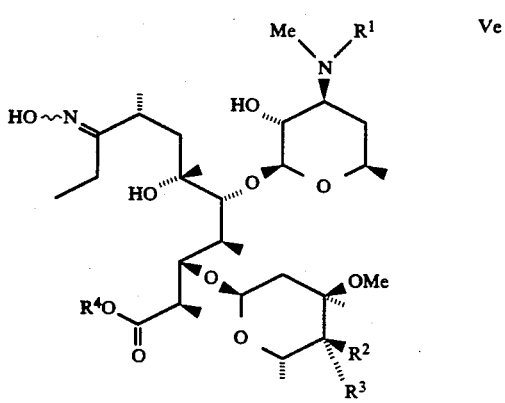

Ve wherein
$R^1$ is hydrogen, methyl, $C_{1-10}$ alkoxycarbonyl or phenylsulfonyl,
one of $R^2$ and $R^3$ is hydrogen and the other is OR, NHR or NMeR where R is hydrogen, $C_{1-10}$ alkyl or phenalkyl,
$R^4$ is hydrogen, $C_{1-10}$ alkyl or phenalkyl;
said method comprising the steps of
(1) cleaving an erythromycin-like compound of the formula where $R^1$, $R^2$, $R^3$ and $R^4$ are as defined above;
(3) converting the oxime product of step (2) to iminoethers VIe and VIIe of the formulae

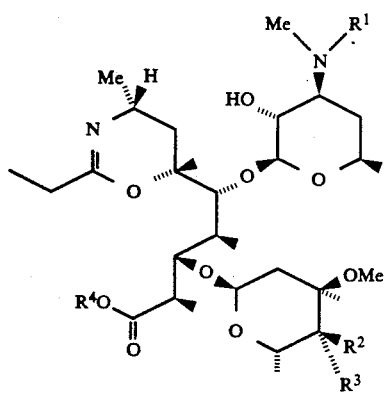   VIe

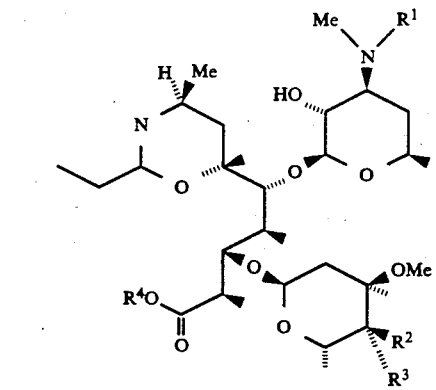   Xe where $R^1$, $R^2$, $R^3$ and $R^4$ are as defined above; and (5) hydrolyzing the aminal products of step (4) to amine products IIIe and IIIf respectively, as defined above.

5. A method of synthesizing amine product compounds of the formulae IIIa and IIIb

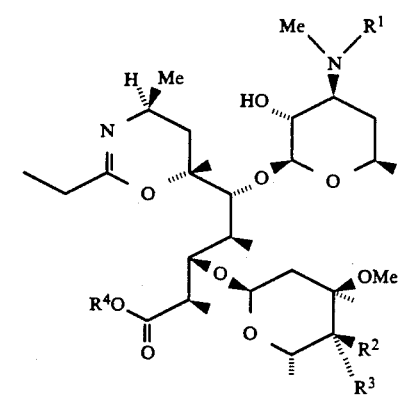   VIIe

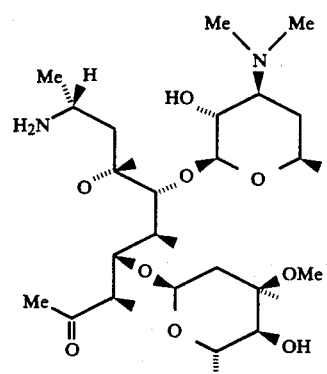   IIIa where $R^1$, $R^2$, $R^3$ and $R^4$ are as defined above;

(4) reducing the iminoether products of step (3) to aminals IXe and Xe, respectively, of the formula

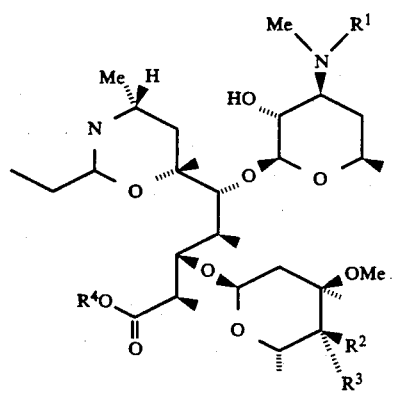   IXe

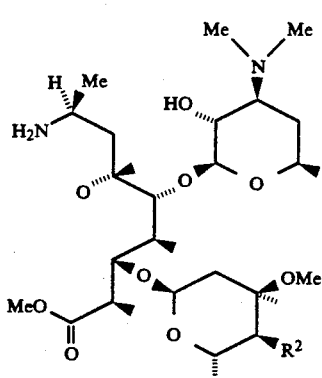   IIIb said method comprising the steps of (1) cleaving erythromycin A to produce compounds of formula IIa and IIb

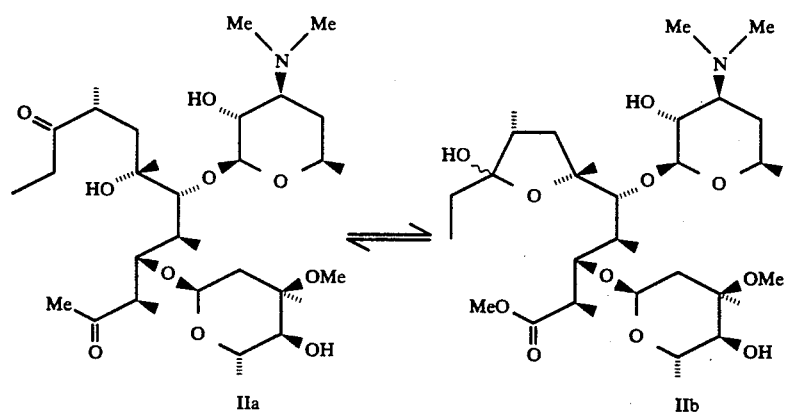
(2) converting the products of step (1) into an oxime Va of the formula
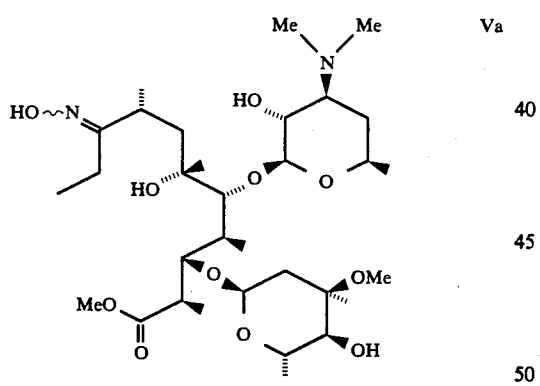
(3) converting the oxime product of step (2) to iminoethers VIa and VIIa of the formulae
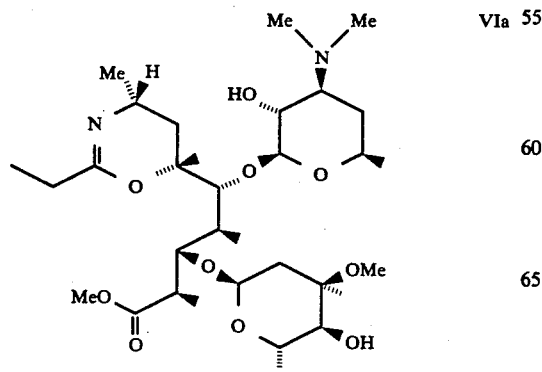
-continued
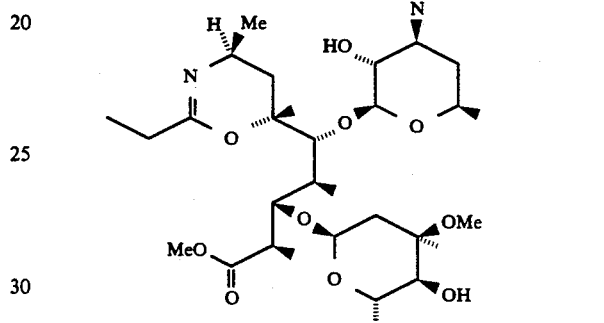
(4) reducing the iminoether products of step (3) to aminals IXa and Xa, respectively, of the formula
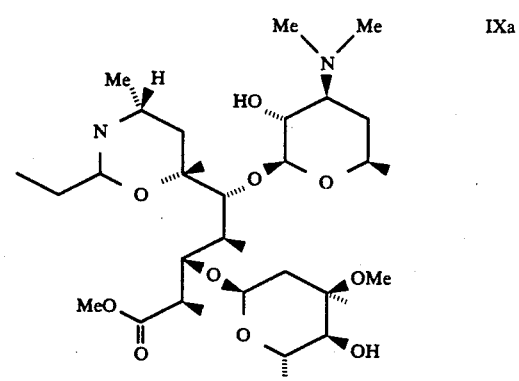
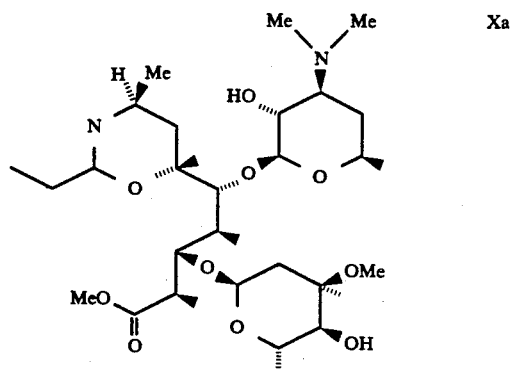
(5) hydrolyzing the aminal products of step (4) to amine products IIIa and IIIb respectively, as defined above.
* * * * *

UNITED STATES PATENT AND TRADEMARK OFFICE
CERTIFICATE OF CORRECTION

PATENT NO. : 5,210,235                                    Page 1 of 3
DATED      : May 11, 1993
INVENTOR(S) : Sherman T. Waddell et al It is certified that error appears in the above-indentified patent and that said Letters Patent is hereby corrected as shown below:

Column 39, between lines 21-37 in claim 1, replace the structure with the following:

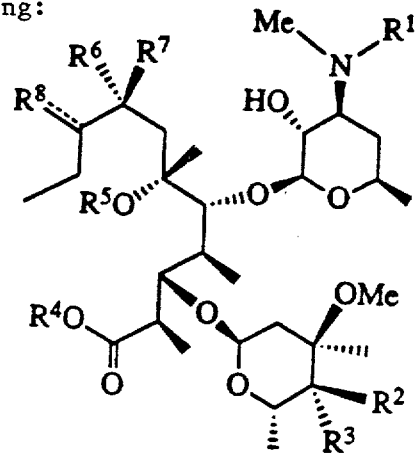

Column 41, betweens lines 1-17 in claim 2m replace the structure with the following:

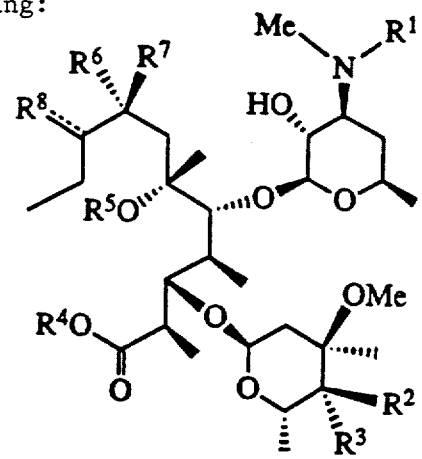

UNITED STATES PATENT AND TRADEMARK OFFICE
CERTIFICATE OF CORRECTION

PATENT NO. : 5,210,235

DATED : May 11, 1993

INVENTOR(S) : Sherman T. Waddell et al

Page 2 of 3

It is certified that error appears in the above-indentified patent and that said Letters Patent is hereby corrected as shown below:

Column 41, between lines 50-66 in claim 3, replace the structure with the following:

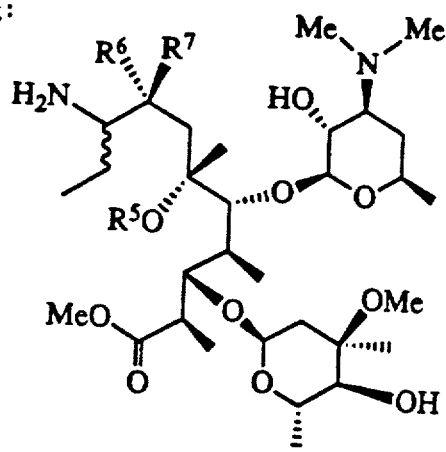

Column 42, between lines 26-41 in claim 3, replace the structure with the following:

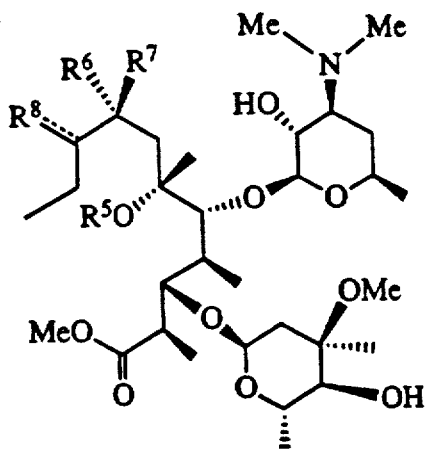

UNITED STATES PATENT AND TRADEMARK OFFICE
CERTIFICATE OF CORRECTION

PATENT NO. : 5,210,235
DATED : May 11, 1993
INVENTOR(S) : Sherman T. Waddell et al It is certified that error appears in the above-indentified patent and that said Letters Patent is hereby corrected as shown below:

Column 46, between lines 48-63, in claim 5, replace the structure with the following:

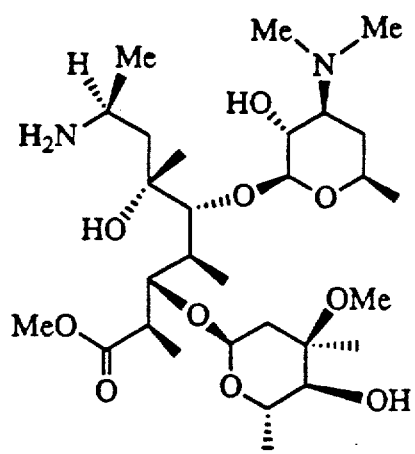

IIIb

Signed and Sealed this

Second Day of August, 1994

Attest:

BRUCE LEHMAN

Attesting Officer    Commissioner of Patents and Trademarks